United States Patent
Harnett et al.

(10) Patent No.: US 9,598,386 B2
(45) Date of Patent: Mar. 21, 2017

(54) IMMUNOMODULATORY COMPOUNDS

(71) Applicants: University of Strathclyde, Glasgow (GB); University of Glasgow, Glasgow (GB)

(72) Inventors: Margaret Harnett, Glasgow (GB); William Harnett, Glasgow (GB); Colin J. Suckling, Glasgow (GB); Fraser Scott, Johnstone (GB); Judith K. Huggan, Kilwinning (GB); Abedawn I. Khalaf, Glasgow (GB)

(73) Assignees: University of Strathclyde, Glasgow (GB); University of Glasgow, Glasgow (GB)

( * ) Notice: Subject to any disclaimer, the term of this patent is extended or adjusted under 35 U.S.C. 154(b) by 0 days.

(21) Appl. No.: 14/420,128

(22) PCT Filed: Jul. 25, 2013

(86) PCT No.: PCT/GB2013/051988
§ 371 (c)(1),
(2) Date: Feb. 6, 2015

(87) PCT Pub. No.: WO2014/023934
PCT Pub. Date: Feb. 13, 2014

(65) Prior Publication Data
US 2015/0218116 A1    Aug. 6, 2015

(30) Foreign Application Priority Data
Aug. 7, 2012 (GB) .................... 1214106.5

(51) Int. Cl.
*C07D 295/088* (2006.01)
*C07D 207/06* (2006.01)
*C07C 317/28* (2006.01)

(52) U.S. Cl.
CPC ........ *C07D 295/088* (2013.01); *C07C 317/28* (2013.01); *C07D 207/06* (2013.01)

(58) Field of Classification Search
CPC .. C07D 295/088; C07D 207/06; C07C 317/28
See application file for complete search history.

(56) References Cited

U.S. PATENT DOCUMENTS 7,078,408 B2 * 7/2006 Neustadt .............. C07D 487/04
514/262.1

FOREIGN PATENT DOCUMENTS

| WO | 2008092049 | | 7/2008 |
|---|---|---|---|
| WO | WO 2008-092049 | * | 7/2008 |
| WO | 2008096128 | | 8/2008 |
| WO | WO 2008-096128 | * | 8/2008 |

OTHER PUBLICATIONS

Tsung et al, Xuaxue Xuebao. 1960, 26, 31-38(only abstract and examples, total of 6 pages supplied).*
Paquette et al., "Unsaturated heterocyclic systems. XL. Evaluation of Spiro[9,10-ethanoanthracene-11,2'-Thietane] S,S-Dioxides and 2.Alpha.-Dialkylanninoalkyl-3-Dialkylaminothietane 1,1-Dioxides as Precursors of 2-Methylenethiete 1,1-Dioxide Derivatives", Aug. 1, 1968, pp. 3020-3027, vol. 33, No. 8, Publisher: The Journal of Organic Chemistry, Published in: http://pubs.acs.org/doi/abs/10.1021/jo01272a003.
Immunology, "Immunology Abstracts", Dec. 3, 2010, pp. 52-190, XP055081493, Published in: http://onlinelibrary.wiley.com/doi/10.1111/j.1365-2567.2010.03390.x/pdf.
ISA/EP, "International Search Report and Written Opinion for the corresponding PCT application GB2013/051988", Oct. 31, 2013, pp. 1-16.

* cited by examiner

*Primary Examiner* — Shailendra Kumar
(74) *Attorney, Agent, or Firm* — Eugene J. Molinelli; Martha Cassidy; Beusse Wolter Sanks & Maire

(57) ABSTRACT

This invention relates to compounds and uses thereof in the treatment or prophylaxis of diseases associated with inflammation.

16 Claims, 8 Drawing Sheets

(C) incidence of CIA score>2

Figure 1:
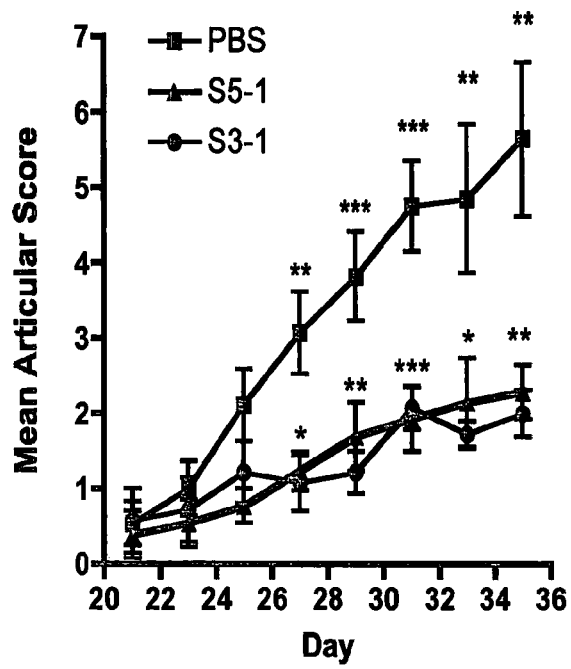
Figure 1:
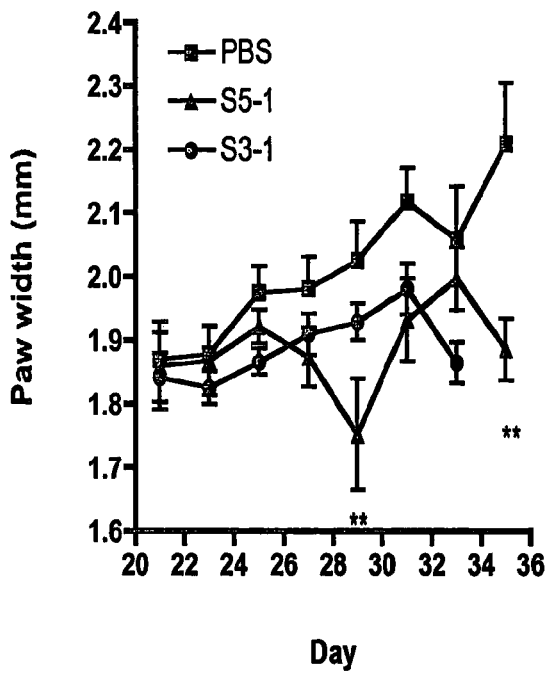
Figure 1:
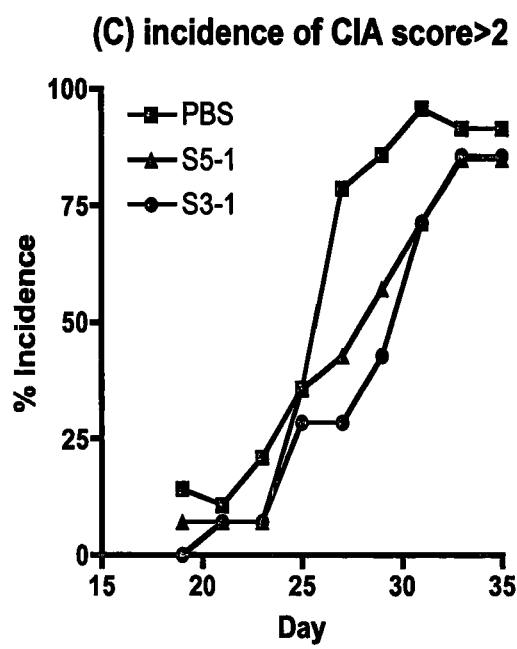
Figure 1:
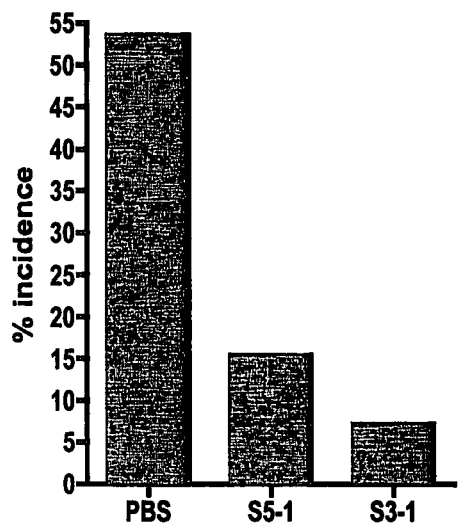

(D) S3-1 & S5-1 suppress incidence of severe CIA (score>4)

PBS

OVA

OVA + S3-1

OVA + S5-1

IMMUNOMODULATORY COMPOUNDS

CROSS-REFERENCE TO RELATED APPLICATIONS

This application is a 371 national stage application of PCT Application No. PCT/GB2013/051988, filed Jul. 25, 2013, and claims the benefit of United Kingdom Application No. 1214106.5, filed on Aug. 7, 2012; the entire contents of which are hereby incorporated by reference as if fully set forth herein.

FIELD OF INVENTION

The present invention relates to compounds and the use thereof in the modulation of inflammation, to suppress the generation of inflammatory mediators for the treatment or prophylaxis of diseases associated with inflammation (anti-inflammatory compounds) such as rheumatoid arthritis (RA) and asthma.

BACKGROUND OF INVENTION

Filarial nematodes are arthropod-transmitted parasites of vertebrates including humans. Infection is long-term with individual worms surviving for in excess of five years. The consensus of opinion amongst workers in this field is that such longevity reflects modulation of the host immune system such that there is a bias in the production of cytokines indicated by reduced production of the pro-inflammatory IFN-γ and increased production of the anti-inflammatory IL-10. There is also a tendency for regulatory components such as regulatory T cells to be present. Overall, the picture is of an immune response demonstrating a somewhat suppressed, anti-inflammatory phenotype, which is often classified as "modified TH-2" ("TH" is derived from a category of T-lymphocyte referred to as "helper"). It has been speculated that such a phenotype is conducive both to parasite survival and host health, the latter by limiting pathology resulting from an over-aggressive immune response. Consistent with this, it is noteworthy that the majority of humans who harbour these parasites demonstrate little evidence of detrimental pathology.

Modulation of the host immune system is likely to involve the active participation of filarial nematodes and hence considerable effort has been spent in characterising the biological properties of molecules secreted by the worms. Goodridge et al. in the Journal of Immunology, 2001, 167: 940-945 and Journal of Immunology, 2005, 174: 284-93 and Whelan et al. in the Journal of Immunology, 2000, 164: 6453-6460, discuss modulation of macrophage and dendritic cell-derived cytokine production by ES-62 resulting in suppression of the production of pro-inflammatory cytokines which may contribute to the immunomodulatory properties of ES-62 that drive the generation of immune responses with an anti-inflammatory and/or TH-2 phenotype. Although these articles provides a rationale for the changes seen in the immune response, no guidance is provided on whether ES-62 may be useful in the clinic for preventing or treating any particular disease(s), in particular those diseases involving inflammation.

Harnett and Harnett in Biochemica et Biophysica Acta, 2001, 1539: 7-15 report investigations into the underlying mechanism of action of ES-62 and it's component, phosphorylcholine (PC). It is concluded that PC has various actions, including a number of immunomodulatory properties similar to those of ES-62. The mechanisms underlying the immunomodulation have not been defined but it has been demonstrated that ES-62 and PC-conjugated proteins mediate their anti-inflammatory actions on macrophages and dendritic cells via the toll-like receptor (TLR), TLR 4 (Goodridge et al. Journal of Immunology, 2005, 174: 284-93 and Goodridge et al. Parasite Immunology, 2007, 29: 127-37). TLR 4, by sensing bacterial lipopolysaccharide (LPS; also known as endotoxin) is a receptor that signals to the immune system that a pathogenic infection is present and that a pro-inflammatory immune response should be mounted. Similarly, related receptors such as TLR2 and TLR9 sense other pathogen products such as bacterial lipopeptide and CpG DNA motifs, respectively, to trigger pro-inflammatory responses. ES-62 and PC-protein conjugates can suppress pro-inflammatory cytokine (IL-6, IL-12 and TNFα) release from macrophages and dendritic cells driven by TLR2, -4 and -9 targeted pathogen products, presumably by subverting their normal pro-inflammatory function.

Collectively, these findings suggested that ES-62 has potential in the mediation of diseases involving an inflammatory response due to the effect of ES-62 on production of inflammatory cytokines. Consistent with this, ES-62 was found to exhibit protective effects in mouse models of rheumatoid arthritis (collagen-induced arthritis; CIA) and asthma (ovalbumin-induced airway hyperresponsiveness) (McInnes et al. 2003 Journal of Immunology 2003 171: 2127-33; Melendez et al. Nature Medicine 2007 13:1375-81). International patent application, publication number WO03024474, describes the clinical use of ES-62 in the treatment of diseases associated with inflammation, such as arthritis. However, in view of the fact that ES-62 is an immunogenic protein and in addition its active moiety results from a helminth-specific post-translational modification, it is not itself appropriate for pharmaceutical application. Thus, since PC, when conjugated to an irrelevant protein such as bovine serum albumin or ovalbumin can mimic the protective effects of ES-62 in CIA (Harnett et al. Ann Rheum Dis 2008 67: 518-23) small molecular compounds having the desired activity are sought, such as non-peptidic small chemical entities based around the structure of the active PC moiety.

The present invention seeks to obviate and/or mitigate the problems seen in the prior art.

In particular, the present invention seeks to provide non-peptide molecules, useful in the treatment of diseases and/or conditions associated with inflammation, such as arthritis, systemic lupus erythematosus, type 1 diabetes, autoimmune hepatitis, psoriasis, inflammatory bowel disease and Crohn's disease, multiple sclerosis, asthma, chronic pulmonary airways disease, in the immune and chemotherapeutic treatment of cancer, in modifying inflammation for the treatment of burns and sepsis, and for use in modifying inflammation in cases of multi-organ failure.

SUMMARY OF THE INVENTION

According to a first aspect of the present invention there is provided a compound according to formula (I), or a physiologically acceptable salt, solvate, ester or other physiologically functional derivative thereof for use in a method of modulating an immune response:

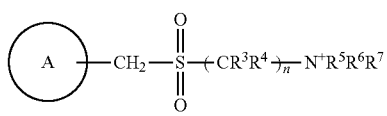

(I)

wherein,
A is an aryl group, optionally substituted by at least one substituent;
where said at least one substituent is independently selected from the group consisting of alkyl, alkenyl, alkynyl, aryl, heteroaryl, carboxy, alkyloxycarbonyl hydroxyl, amino, nitro, alkyloxy, perfluoroalkyloxy, —SH, alkylthio, formyl, cyano, carbamoyl, an amide, halo, a ketone, —S(O)NR$^{12}$R$^{13}$ or —S(O)R$^{14}$; wherein R$^{12}$, R$^{13}$ or R$^{14}$ are independently selected from the group consisting of H, alkyl, alkenyl, alkynyl, or substituted or unsubstituted monocyclic or polycyclic aryl or heteroaryl;
wherein when one of R$^5$, R$^6$ and R$^7$ is absent, the nitrogen atom to which they are bonded is not charged or when R$^5$, R$^6$ and R$^7$ are present together the nitrogen atom to which they are bonded is positively charged and there is present a negatively charged counter ion;
R$^3$, R$^4$, R$^5$, R$^6$ and R$^7$ when present are independently, for each occurrence, selected from the group consisting of H, alkyl, alkenyl and alkynyl; and optionally, two or more of R$^5$, R$^6$ and R$^7$ are bonded together to form a monocyclic or bicyclic ring with the nitrogen atom to which they are bonded; and
n is an integer having a value of from 1 to 6.

Preferably A is a 5 or 6 membered cyclic or heterocyclic ring structure, or bicyclic ring. When heterocyclic, the ring may include one or more of N, S or O. More preferably, A is a 6 membered cyclic or heterocyclic ring, such as a phenyl group. A may be more preferably substituted with an alkyl (such as a methyl), carboxy, alkyloxycarbonyl hydroxyl, amino, nitro, alkyloxy, —SH, alkylthio, formyl, cyano, carbamoyl, or halo (such as bromo).

In a preferred embodiment there is provided a compound of formula (II) or a physiologically acceptable salt, solvate, ester or other physiologically functional derivative thereof for use in therapy:

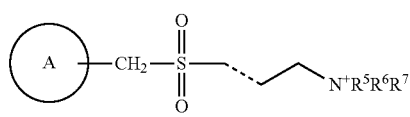

(II)

wherein
A is an phenyl group, optionally substituted by at least one substituent;
wherein said at least one optional substituent is independently selected from the group consisting of alkyl, carboxy, alkyloxycarbonyl hydroxyl, amino, nitro, alkyloxy, —SH, alkylthio, formyl, cyano, carbamoyl, halo;
the dashed bond is present or absent;
wherein when one of R$^5$, R$^6$ and R$^7$ is absent, the nitrogen atom to which they are bonded is not charged and both remaining R groups are not H, or when R$^5$, R$^6$ and R$^7$ are present together the nitrogen atom to which they are bonded is positively charged and there is present a negatively charged counter ion;

R$^5$, R$^6$ and R$^7$, when present are independently, for each occurrence, selected from the group consisting of H, and alkyl; and optionally, two or more of R$^5$, R$^6$ and R$^7$ are bonded together to form a monocyclic ring with the nitrogen atom to which they are bonded.

In the compounds according to formula I and II, the ring structure A/phenyl group may in certain embodiments be, when substituted, substituted in the para-, or meta-positions.

In a further preferred embodiment there is provided a compound of formula (III) or a physiologically acceptable salt, solvate, ester or other physiologically functional derivative:

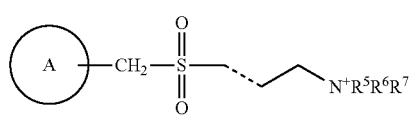

(III)

wherein
A is an phenyl group, substituted by at least one substituent;
wherein said at least one optional substituent is independently selected from the group consisting of alkyl, and halo;
the dashed bond is present or absent;
wherein when one of R$^5$, R$^6$ and R$^7$ is absent, the nitrogen atom to which they are bonded is not charged and both remaining R groups are not H, or when R$^5$, R$^6$ and R$^7$ are present together the nitrogen atom to which they are bonded is positively charged and there is present a negatively charged counter ion; and
R$^5$, R$^6$ and R$^7$, when present are independently, for each occurrence, selected from the group consisting of H, and alkyl; and optionally, two or more of R$^5$, R$^6$ and R$^7$ are bonded together to form a monocyclic ring with the nitrogen atom to which they are bonded.

More preferably the substituent is a $C_1$-$C_4$ alkyl, such as methyl, or a halo, such as bromo.

In the compounds according to formula I, II and III, when R$^5$, R$^6$ and R$^7$ are present, they are each preferably $C_1$-$C_4$ alkyl, such as methyl.

Alternatively two of R$^5$, R$^6$ or R$^7$ form a pyrrolidine ring or a morpholine ring with the nitrogen atom, and the remainder one of R$^5$, R$^6$ or R$^7$ is a methyl group or is absent.

In accordance with the formulae described above when R$^5$, R$^6$ or R$^7$ are present, the nitrogen to which they are bonded is positively charged and negatively charged counter ion is selected from the group consisting of chloride (Cl$^-$), bromide (Br$^-$), iodide (I$^-$) fluoride (F$^-$), and methanesulphonate (SO$_3^-$CH$_3$).

The compounds according to formula (I) (II) or (III) or a physiologically acceptable salt, solvate, ester or other physiologically functional derivative thereof, may be used in the treatment or prophylaxis of inflammatory diseases in an animal. The animal requiring treatment or prophylaxis is usually a human or non-human mammal.

According to the present invention, there is provided a compound according to formula (I), (II), or (III), or a physiologically acceptable salt, solvate, ester or other physiologically functional derivative thereof, for use medicine, such as in the modulation of an immune response, such as in the treatment or prophylaxis of inflammatory diseases in an animal.

The animal requiring treatment or prophylaxis is usually a human or non-human mammal.

Many diseases involve inflammation, and particularly relevant diseases for treatment or prophylaxis according to the present invention are autoimmune diseases such as type 1 diabetes mellitus, rheumatoid arthritis (RA), systemic lupus erythematosus (SLE), psoriasis, multiple sclerosis (MS), autoimmune hepatitis, sarcoidosis, inflammatory bowel disease, Crohn's disease, asthma, chronic obstructive pulmonary disease (chronic pulmonary airways disease) and atherosclerosis.

The present invention has particular application for the treatment or prophylaxis of rheumatoid arthritis and asthma.

The present invention further finds uses in settings where inflammation is to be modified such as in the other inflammatory disorders listed above and also for the treatment of burns and sepsis, and for use in modifying inflammation in cases of multi-organ failure.

According to a third aspect of the present invention there is provided the use of a compound according to formula (I), (II), or (III) or a physiologically acceptable salt, solvate, ester or other physiologically functional derivative thereof, for the manufacture of a medicament for modulating an immune response, such as in the treatment or prophylaxis of inflammatory disease.

In a fourth aspect of the present invention there is provided a method for modulating an immune response, such as in the treatment or prophylaxis of inflammatory disease in an animal comprising administering to said animal a therapeutically or prophylactically effective amount of a compound according to formula (I), (II), or (III) or a physiologically acceptable salt, solvate, ester or other physiologically functional derivative thereof.

In the compounds described herein, an alkyl group may be independently a $C_1$-$C_{22}$ alkyl, preferably $C_1$-$C_4$ alkyl, for example, methyl, ethyl, propyl, butyl.

An alkenyl group may be independently a $C_2$-$C_{10}$ alkenyl, preferably $C_2$-$C_4$ alkenyl.

An alkynyl group may be independently a $C_2$-$C_{10}$ alkynyl, preferably $C_2$-$C_4$ alkynyl.

The alkyl, alkenyl or alkynyl groups may be branched, unbranched, linear or cyclic and may be substituted or unsubstituted.

For example typical branched alkyl groups include iso-propyl, iso-butyl, sec-butyl, tert-butyl, 3-methylbutyl, 3,3-dimethylbutyl and variations, including isomers thereof.

As described herein, the alkyl, alkenyl or alkynyl groups may be substituted, and the substituents may be any chemical moiety such as a hydroxyl, substituted or unsubstituted amine, substituted or unsubstituted amide, halide (such as fluoro, chloro, bromo, iodo), alkoxy, thio, nitro, carboxy, an ester, cyano, or aryl (such as phenyl, naphthyl and pyridyl).

The geometry of the double bonds in the alkenyl groups may be in the cis- or trans-geometry.

Examples of physiologically acceptable salts of the compounds described herein include acid addition salts formed with organic carboxylic acids such as acetic, lactic, tartaric, maleic, citric, pyruvic, oxalic, fumaric, oxaloacetic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids.

Physiologically functional derivatives of the compounds described herein are derivatives that can be converted in the body into the parent compound. Such physiologically functional derivatives may also be referred to as "pro-drugs" or "bioprecursors". Physiologically functional derivatives of compounds of the present invention include in vivo hydrolysable esters.

It may be convenient or desirable to prepare, purify, and/or handle a corresponding solvate of the compounds described herein, which may be used in the any one of the uses/methods described. The term solvate is used herein to refer to a complex of solute, such as a compound or salt of the compound, and a solvent. If the solvent is water, the solvate may be termed a hydrate, for example a mono-hydrate, di-hydrate, tri-hydrate etc, depending on the number of water molecules present per molecule of substrate.

It will be appreciated that some of the compounds of the present invention may exist in various stereoisomeric forms and the compounds of the present invention as hereinbefore defined include all stereoisomeric forms and mixtures thereof, including enantiomers and racemic mixtures. The present invention includes within its scope the use of any such stereoisomeric form or mixture of stereoisomers, including the individual enantiomers of the compounds of formulae (I), (II) or (III) as well as wholly or partially racemic mixtures of such enantiomers.

For use according to the present invention, a compound according to formulae (II), or (III) or a physiologically acceptable salt, solvate, ester or other physiologically functional derivative thereof, is preferably presented together with one or more pharmaceutically acceptable carriers to provide a pharmaceutical formulation. Optionally other therapeutic and/or prophylactic ingredients may be included in the pharmaceutical formulation. The carrier(s) must be acceptable in the sense of being compatible with the other ingredients of the formulation and not deleterious to the recipient thereof.

Pharmaceutical formulations include those suitable for oral, topical (including dermal, buccal and sublingual), rectal or parenteral (including subcutaneous, intradermal, intramuscular and intravenous), nasal and pulmonary administration e.g., by inhalation. The formulation may, where appropriate, be conveniently presented in discrete dosage units and may be prepared by any of the methods well known in the art of pharmacy. All methods include the step of bringing into association an active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of active compound. A tablet may be made by compression or moulding, optionally with one or more accessory ingredients. Compressed tablets may be prepared by compressing in a suitable machine an active compound in a free-flowing form such as a powder or granules optionally mixed with a binder, lubricant, inert diluent, lubricating agent, surface-active agent or dispersing agent. Moulded tablets may be made by moulding an active compound with an inert liquid diluent. Tablets may be optionally coated and, if uncoated, may optionally be scored. Capsules may be prepared by filling an active compound, either alone or in admixture with one or more accessory ingredients, into the capsule shells and then sealing them in the usual manner. Cachets are analogous to capsules wherein an active compound together with any accessory ingredient(s) is sealed in a rice paper envelope. An active compound may also be formulated as dispersible granules, which may for example be suspended in water before administration, or sprinkled on food. The granules may be packaged, e.g., in a sachet. Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active compound is formulated in an appropriate release-controlling matrix, or is coated with a suitable release-controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active compound with the softened or melted carrier(s) followed by chilling and shaping in moulds.

Pharmaceutical formulations suitable for parenteral administration include sterile solutions or suspensions of an active compound in aqueous or oleaginous vehicles.

Injectable preparations may be adapted for bolus injection or continuous infusion. Such preparations are conveniently presented in unit dose or multi-dose containers that are sealed after introduction of the formulation until required for use. Alternatively, an active compound may be in powder form, which is constituted with a suitable vehicle, such as sterile, pyrogen-free water, before use.

An active compound may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing an active compound and desirably having a diameter in the range of 0.5 to 7 microns are delivered in the bronchial tree of the recipient.

As one possibility such formulations are in the form of finely comminuted powders which may conveniently be presented either in a pierceable capsule, suitably of, for example, gelatin, for use in an inhalation device, or alternatively as a self-propelling formulation comprising an active compound, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active compound is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microliters, upon each operation thereof.

As a further possibility an active compound may be in the form of a solution or suspension for use in an atomizer or nebuliser whereby an accelerated airstream or ultrasonic agitation is employed to produce a fine droplet mist for inhalation.

Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension.

It should be understood that in addition to the aforementioned carrier ingredients the pharmaceutical formulations described above may include, an appropriate one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

Pharmaceutically acceptable carriers are well known to those skilled in the art and include, but are not limited to, 0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Therapeutic formulations for veterinary use may conveniently be in either powder or liquid concentrate form. In accordance with standard veterinary formulation practice, conventional water-soluble excipients, such as lactose or sucrose, may be incorporated in the powders to improve their physical properties. Thus particularly suitable powders of this invention comprise 50 to 100% w/w and preferably 60 to 80% w/w of the active ingredient(s) and 0 to 50% w/w and preferably 20 to 40% w/w of conventional veterinary excipients. These powders may either be added to animal feedstuffs, for example by way of an intermediate premix, or diluted in animal drinking water.

Liquid concentrates of this invention suitably contain the compound according to formula (I) or a physiologically acceptable salt, solvate, ester or other physiologically functional derivative thereof, and may optionally include a veterinary acceptable water-miscible solvent, for example polyethylene glycol, propylene glycol, glycerol, glycerol formal or such a solvent mixed with up to 30% v/v of ethanol. The liquid concentrates may be administered to the drinking water of animals.

DETAILED DESCRIPTION OF THE INVENTION

The present invention will now be further described by way of example and with reference to figures that show:

FIG. 1 shows S3 & S5 suppress collagen-induced arthritis (CIA). DBA/1 mice undergoing CIA (PBS) were treated with SMAs S3 (1 μg/dose; S3-1) and S5 (1 μg/dose; S5-1) at d-2, d0 and d21 and monitored every second day for (A) articular score; (B) paw swelling; (C) incidence of CIA (articular score>2) and (D) incidence of severe pathology (articular score >4). Data in A & B are presented as mean values±SEM where PBS, n=28, S3, n=14 and S5, n=13 individual mice, except at d33 and d35 where PBS, n=14, S3, n=7 and S5, n=7 individual mice, and analysis was by Mann-Whitney test and *p<0.05, p<0.01 and *p<0.001 where blue * and black * represent PBS versus S3-1 and S5-1, respectively.

Figure 2:
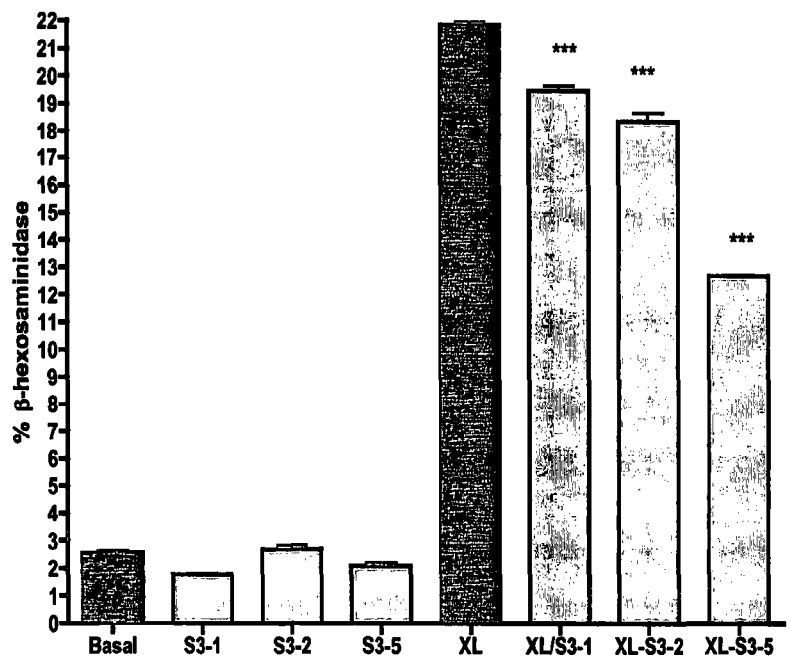
Figure 2:
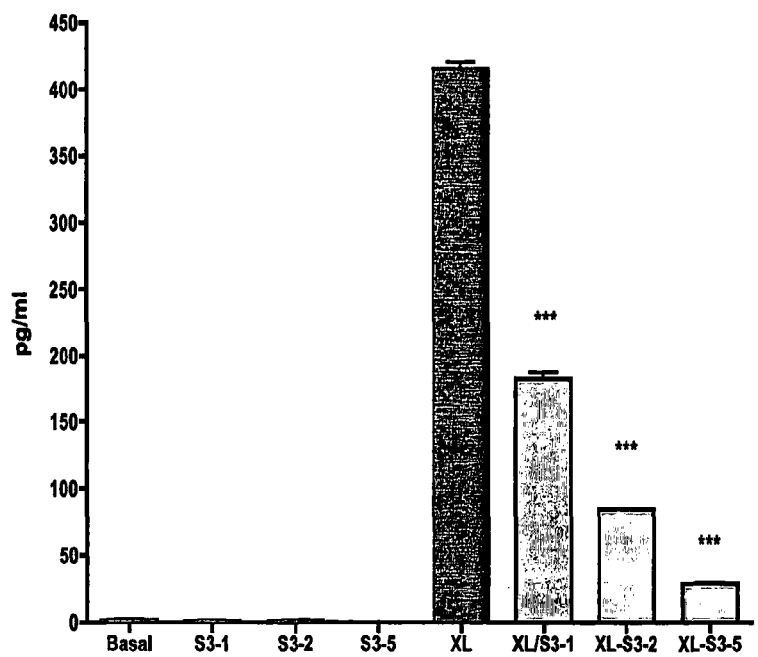
Figure 2:
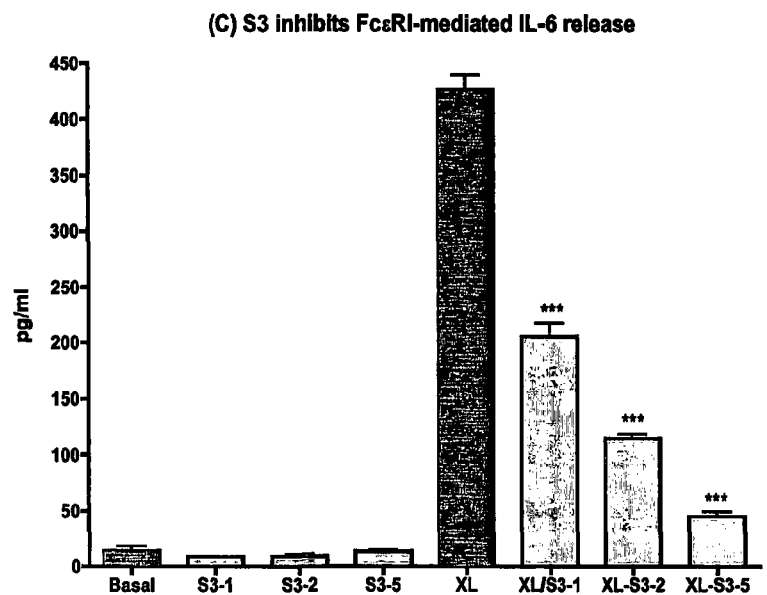
Figure 2:
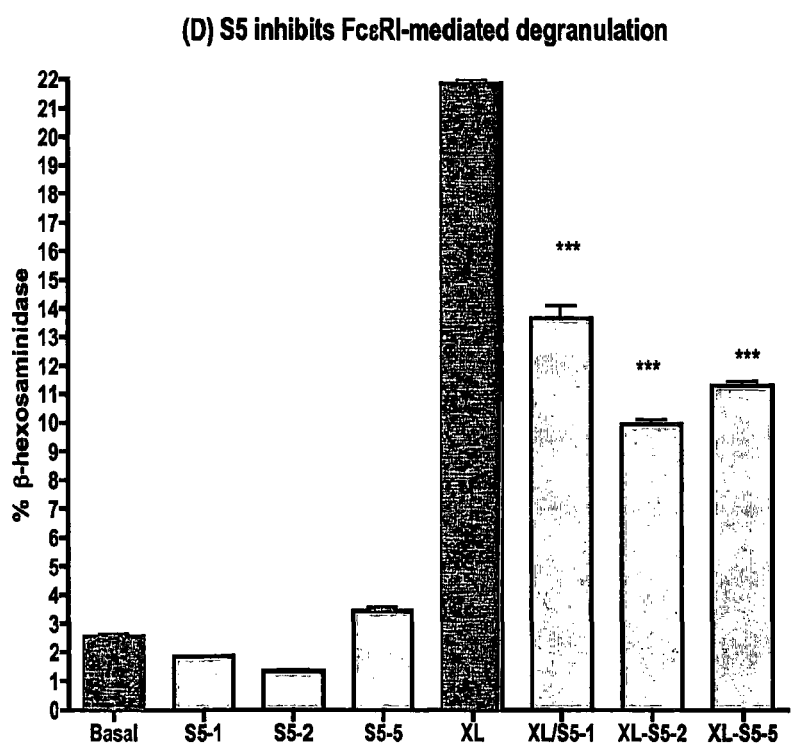
Figure 2:
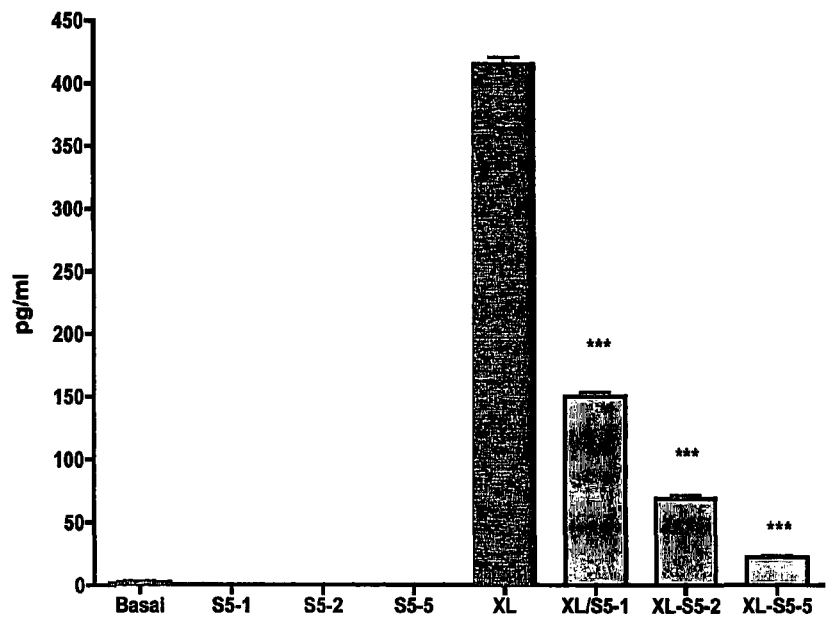
Figure 2:
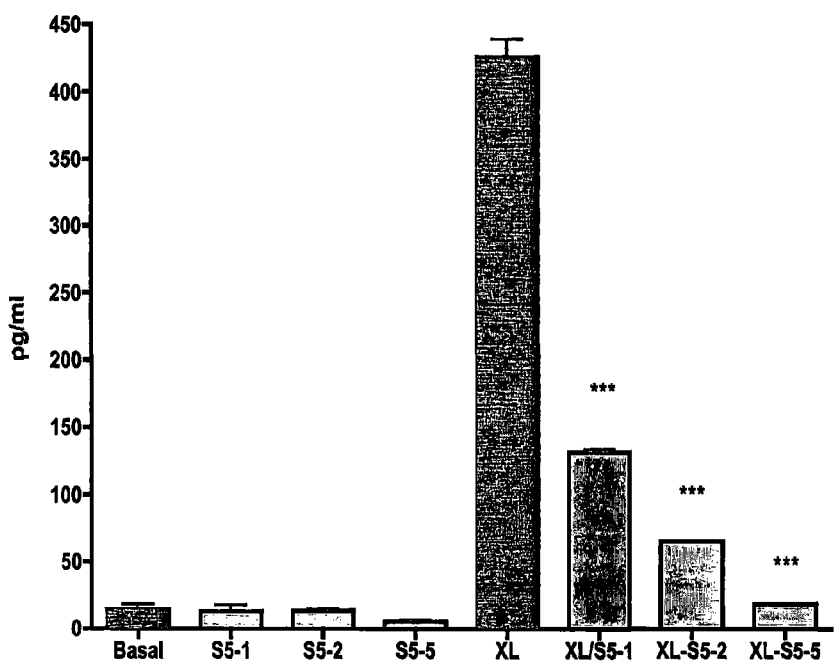
Figure 3A:
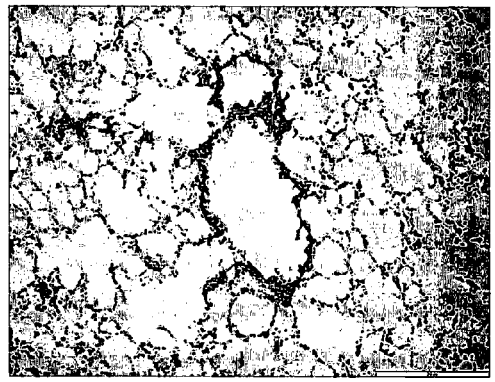
Figure 3A:
Figure 3A:
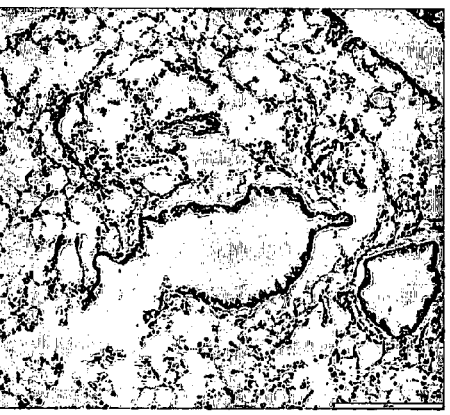
Figure 3A:
Figure 3B:
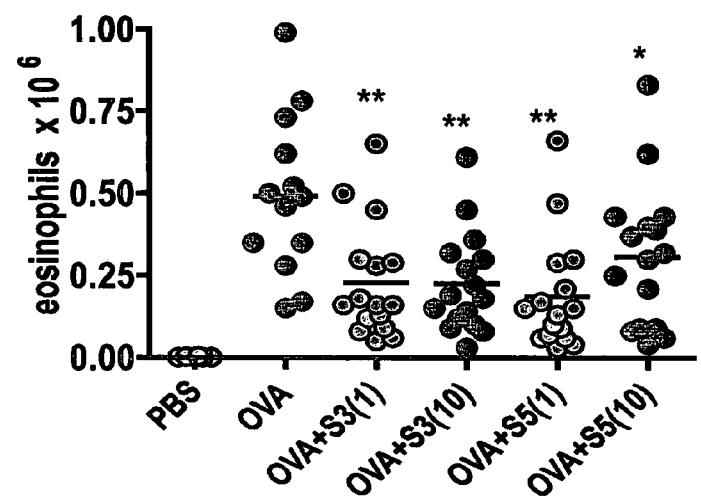
Figure 3B:
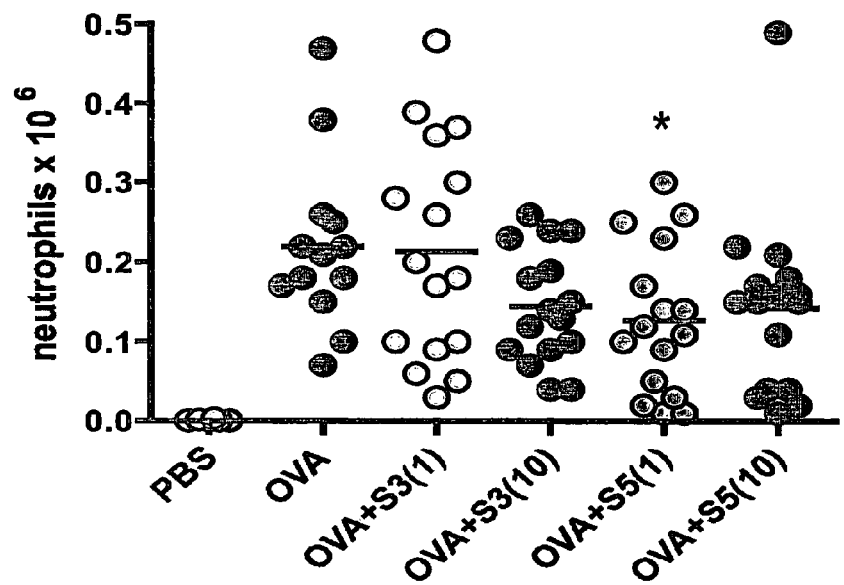
Figure 3C:
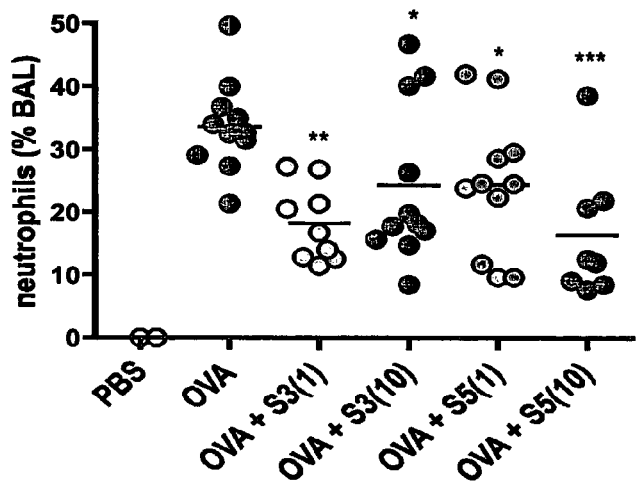
Figure 3C:
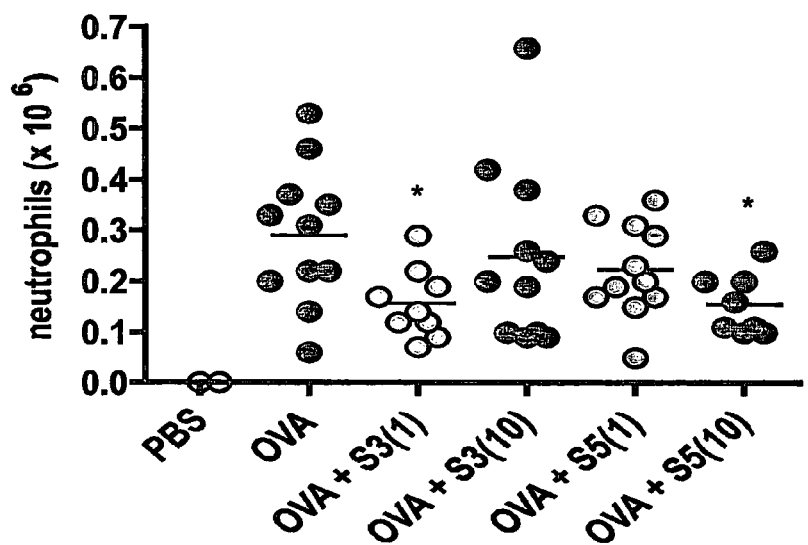

FIG. 2 shows S3 and S5 inhibit mast cell degranulation and cytokine production. Peritoneal-derived mast cells (PDMC; panels A & D) or bone marrow-derived mast cells (BMM; B, C, E & F) were pre-treated with the indicated concentrations of S3 and S5 (μg/ml) during the IgE sensitisation phase and then degranulation measured 1 h (A & D) following crosslinking of the IgE-bound FcεRI receptors (XL) or not (Basal). Alternatively TNFα (B & E) or IL-6 (C & F) release was measured 24 h following FcεRI crosslinking. Data are presented as means±SD where n=3 and analysis is by 1-way ANOVA and Newman-Keuls post test where ***p<0.001.

FIG. 3 shows that prophylactic treatment with S3 and S5 inhibits lung pathology as indicated by H & E staining of lung tissue (A) and eosinophil and (to a degree) neutrophil influx into the lungs (BALF; B) Therapeutic treatment with S3 and S5 inhibits neutrophil influx into the lungs (BALF; C)

MATERIALS, METHODS AND RESULTS

Compounds were synthesised according to the following methods, with reference to the depicted schemes and experimental data.

All starting materials were bought from Aldrich with the exception of choline iodide, which was bought from Lancaster. Starting materials were used without further purification.

Abbreviations:
DMF Dirnethylformamide
DCM Dichloromethane
m-CPBA meta-chloroperbenzoic acid
NEt$_3$ Triethyl amine
TLC Thin layer chromatography
NMR Nuclear magnetic resonance
HPLC High performance liquid chromatography
IR Infra red
mp Melting point
LC-MS Liquid chromatography mass spectroscopy
HR-MS High resolution mass spectroscopy
EtOAc Ethyl acetate
TFA Trifluoroacetic acid Intermediates 2-[(4-Bromobenzyl)sulfonyl]ethanol 1-Bromo-4-(bromomethyl)benzene (10.00 g, 40.00 mmol), 2-mercaptoethanol (3.13 g, 40.00 mmol) and K$_2$CO$_3$ (5.53 g, 40.00 mmol, anhydrous) were added to DCM (50 mL, dry) at room temperature with stirring. The stirring was continued for 48 h after which water was added and then the reaction was extracted with DCM. The organic layer was collected, dried (MgSO$_4$), filtered, and the solvent removed under reduced pressure to give the required product as a pale yellow oil (11.00 g, 99%).

$^1$H-NMR (CDCl$_3$): 7.46-7.44 (2H, d, 2×C(2)H), 7.22-7.20 (2H, d, 2×C(3)H), 3.71 (2H, s, C(5)H$_2$), 3.70-3.68 (2H, t, C(7)H$_2$), 2.65-2.62 (2H, t, C(6)H$_2$), 1.93 (1H-1, br, s, OH).

$^{13}$C-NMR (CDCl$_3$): 137.41 (C-4), 131.99 (C-2), 130.80 (C-3), 121.32 (C-1), 60.60 (C-7), 35.48 (C-5), 34.65 (C-6).

IR (NaCl): 3390 (br), 2919, 1901, 1663, 1589, 1486, 1402, 1289, 1198, 1096, 1069, 1011, 881, 821 cm$^{-1}$

HR-MS: For C$_9$H$_{11}$BrOS requires 245.9714/247.9693. found 245.9712/245.9692.

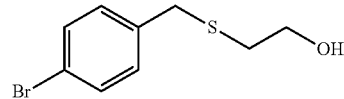 [SMILES: OCCSCc1ccc(Br)cc1]

2-[(4-Bromobenzyl)sulfonyl]ethanol

2-[(4-Bromobenzyl)sulfonyl]ethanol (11.00 g, 44.7 mmol) was dissolved in DCM (50 mL, dry) to which m-CPBA (21.10 g, 122.3 mmol) was added at room temperature with stirring. The reaction was slightly exothermic. The reaction mixture was left stirring at room temperature overnight. 15 minutes after the addition of m-CPBA a white solid material precipitated. NaHCO$_3$ (saturated) was added and the reaction mixture was extracted. The organic layer was extracted with brine and collected, dried (MgSO$_4$), filtered, and the solvent removed under reduced pressure. The crude product was applied to a gel column chromatography using ethyl acetate/n-hexane 1/1, R$_F$=0.1 to give the pure material as white crystals (4.47 g, 36%) after recrystallization from ethyl acetate/n-hexane, mp 97-99° C.

$^1$H-NMR (DMSO-d$_6$): 7.61-7.59 (2H, d, 2×C(2)H), 7.37-7.35 (214, d, 2×C(3)H), 5.21 (1H, br s, OH), 4.48 (2H, s, C(5)H$_2$), 3.83-3.80 (2H, t, C(7)H$_2$), 3.18-3.15 (2H, t, C(6)H$_2$).

$^{13}$C-NMR (DMSO-d$_6$): 133.21 (C-3), 131.38 (C-2), 128.14 (C-1), 121.89 (C-4), 58.86 (C-7), 54.90 (C-6), 53.99 (C-5).

IR (KBr): 3480 (br), 2991, 2928, 1490, 1408, 1388, 1291, 1262, 1235, 1115 (s), 1064, 1014, 848, 808, 705, 523 cm$^{-1}$

HR-MS: For C$_9$H$_{11}$BrO$_3$S requires 277.9612/279.9592. found 277.9614/279.9586.

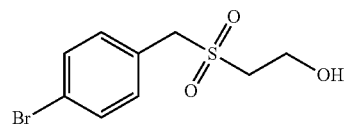 [SMILES: O=S(=O)(CCO)Cc1ccc(Br)cc1]

1-Bromo-4-[(vinylsulfonyl)methyl]benzene

2-[(4-Bromobenzyl)sulfonyl]ethanol (2.00 g, 7.17 mmol) was dissolved in DCM (25 mL, dry) to which triethylamine (3 mL, 2.18 g, 21.52 mmol, 3.0 molar equivalent, anhydrous) was added followed by methylsulphonyl chloride (2 mL, 3.12 g, 19.14 mmol, 2.7 molar equivalent) at 0° C. with stirring, which was continued at room temperature overnight. The reaction mixture was basified with sodium hydrogen carbonate (saturated). The organic layer was collected after the extraction, dried over (MgSO$_4$), filtered and the solvent removed under reduced pressure. The crude product was applied to a silica gel column chromatography using ethyl acetate/n-hexane (1/2, R$_F$=0.4). The required product (1.600 g, 86%) was obtained as white solid, mp 95-97° C.

$^1$H-NMR (DMSO-d$_6$): 7.60-7.58 (2H, d, 2×C(2)H), 7.32-7.30 (2H, d, 2×C(3)H), 6.96-6.89 (1H, dd, C(6)H, J=16.8 Hz, J=9.9 Hz), 6.21-6.19 (1H, d, C(7)H, J=8 Hz), 6.09-6.05 (1H, d, C(8)H, J=16.6 Hz), 4.55 (2H, s, C(5)H$_2$).

$^{13}$C-NMR (DMSO-d$_6$): 136.24 (C-4), 133.11 (C-2), 131.34 (C-3), 130.50 (C-6), 128.11 (C-1), 121.91 (C-7), 58.05 (C-5).

IR (KBr): 3437, 3057, 2981, 2932, 1489, 1408, 1309, 1260, 1161, 1121, 1072, 1014, 976, 843, 795, 714, 519 cm$^{-1}$

HR-MS: Found 259.9506/261.9484 for C$_9$H$_9$BrO$_2$S requires 259.9507/261.9486.

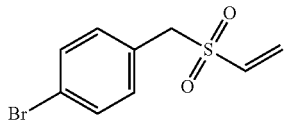

2-[(4-Methyl benzyl)sulfanyl]ethanol 1-(Bromomethyl)-4-methylbenzene (10.00 g, 54.03 mmol), 2-mercaptoethanol (4.22 g, 54.03 mmol) and K$_2$CO$_3$ (7.47 g, 54.03 mmol, anhydrous) were added to DCM (50 mL, dry) at room temperature with stirring. The stirring was continued for 48 h. Water was added and the reaction mixture was extracted with DCM. The organic layer was collected, dried (MgSO$_4$), filtered, and the solvent removed under reduced pressure to give the required product as a pale yellow oil (9.60 g, 98%).

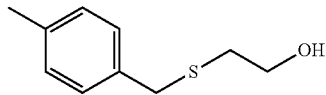

$^1$H-NMR (DMSO-d$_6$): 7.23-7.21 (2H, d, 2×C(3)H), 7.14-7.12 (2H, d, 2×C(2)H), 4.79-4.76 (1H, t, OH), 3.72 (2H, s, C(6)H$_2$), 3.57-3.52 (2H, m, C(8)H$_2$), 2.52-2.48 (2H, t, C(5)H$_2$), 2.30 (3H, s, C(1)H$_3$).

$^{13}$C-NMR (DMSO-d6): 135.77 (C-2), 135.66 (C-5), 128.84 (C-3), 128.70 (C-4), 60.63 (C-8), 35.03 (C-6), 33.33 (C-7), 20.62 (C-1).

IR (KBr): 3390 (br), 2920, 2868, 1664, 1513, 1422, 1386, 1098, 1068, 1020, 878, 817, 726 cm$^{-1}$

HR-MS: For C$_{10}$H$_{14}$OS requires 182.07654. found 182.0764.

Reference: Czobor, Francisc; Cristescu, Carol. as-Triazine derivatives with potential therapeutic action. Part XXIX. Synthesis of 5-[2-(halogenobenzylthio)-ethyl]thio-6-azauracil derivatives as potential antiviral agents. Revue Roumaine de Chimie (2002), 46(9), 1007-1011.

2-[(4-Methyl benzyl)sulfonyl]ethanol

2-[(4-Methylbenzyl)sulfanyl]ethanol (9.60 g, 52.7 mmol) was dissolved in DCM (50 mL, dry) to which m-CPBA (18.18 g, 105.0 mmol, 2.0 molar equivalent) was added at room temperature with stirring. The reaction was slightly exothermic. The reaction mixture was left stirring at room temperature overnight. 15 minutes after the addition of m-CPBA a white solid material precipitated. NaHCO$_3$ (saturated) was added and the reaction mixture was extracted. The organic layer was extracted with brine and collected, dried (MgSO$_4$), filtered, and the solvent removed under reduced pressure. The crude product was recrystallized from ethyl acetate/n-hexane to give the pure material as white crystals (3.11 g). The mother liquor was applied to a silica gel column chromatography using ethyl acetate/n-hexane 1/1; (R$_F$=0.2 & R$_F$=0.5) to give an additional amount (0.40 g). The total amount obtained was (3.51 g, 31%), mp 102-104° C.

$^1$H-NMR (DMSO-d$_6$): 7.30-7.28 (2H, d, 2×C(3)H), 7.21-7.19 (2H, d, 2×C(4)H), 5.29 (1H, br, s, OH), 4.41 (2H, s, C(6)H$_2$), 3.82-3.79 (2H, t, C(8)H$_2$), 3.14-3.11 (2H, t, C(7)H$_2$), 2.31 (3H, s, C(1)H$_3$).

$^{13}$C-NMR (DMSO-d6): 137.66 (C-2), 130.94 (C-4), 128.99 (C-3), 125.63 (C-5), 59.32 (C-6), 54.90 (C-7), 53.71 (C-8), 20.70 (C-1).

IR (KBr): 3480 (br), 2898, 2925, 2891, 1697, 1517, 1419, 1296 (s), 1263, 1175, 1116 (s), 1063, 1012, 848, 549, 489 cm$^{-1}$.

HR-MS: Found 214.0665 for C10H14O3S requires 214.0664.

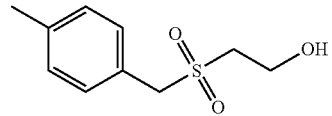

2-[(4-Methylbenzyl)sulfonyl]ethyl methanesulfonate and 1-methyl-4-[(vinylsulfonyl)methyl]benzene 2-[(4-Methylbenzyl)sulfonyl]ethanol (3.110 g, 14.51 mmol) was dissolved in DCM (25 mL, dry) to which triethylamine (2.202 g, 21.77 mmol, 1.5 molar equivalent, anhydrous) was added, followed by methylsulphonyl chloride (2.493 g, 21.77 mmol, 1.5 molar equivalent) at 0° C. with stirring, which was continued at room temperature overnight. The reaction mixture was basified with sodium hydrogen carbonate (saturated). The organic layer was collected after the extraction, dried over (MgSO$_4$), filtered and the solvent removed under reduced pressure. The crude product was obtained as yellow semi-solid (5.060 g). TLC showed two spots: R$_F$=0.3 & R$_F$=0.6 (ethyl acetate/n-hexane 1/1. This mixture was used in the next step without further purification.

$^1$H-NMR (DMSO-d6): 7.30-7.28 (1H, d, 2×C-4H), 7.24-7.21 (3H, overlapping doublets, 2×C—CH, 2×C-3H), 7.18-7.16 (2H, d, 2×C-DH), 6.95-6.88 (1H, dd, C-GH, J=9.9 Hz, C-GI, J=16.6 Hz), 6.18-6.16 (2I-1, d, C—HH, J=9.9 Hz), 6.08-6.04 (2H, d, C—IH, J=16.6 Hz), 4.54-4.52 (1H, t, C-8H$_2$), 4.49 (1H, s, C-6H$_2$), 4.45 (2H, s, C—FH$_2$), 3.56-3.53 (IH, t, C-7H$_2$), 3.26 (1.5H, s, C-9H$_3$), 2.31 (1.5H, s, C-1H$_3$), 2.29 (3H, s, C-AH$_3$).

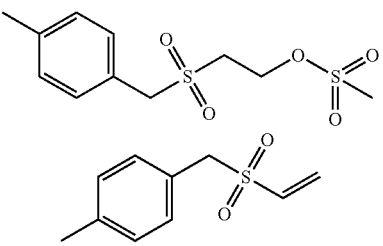

3-(4-Methylbenzylthio)propan-1-ol 3-(4-Methylbenzylthio)propan-1-ol (1.46 g, 7.46 mmol) was dissolved in DCM (20 ml, anhydrous) to which was added a solution of m-CPBA (2.80 g, 16.2 mmol, 2.17 eq.)

in DCM (30 ml, anhydrous) at 0° C., under nitrogen The reaction mixture was allowed to warm to room temperature and stirring was continued for a further 24 h. After this time, the resulting white precipitate was filtered under vacuum and the filtrate was washed with NaHCO$_3$ (2×100 ml) and DCM (100 ml). The organic extracts were combined, dried over MgSO$_4$ and concentrated under reduced pressure to leave colourless oil which crystallised to a white solid upon standing. This was then dried at room temperature under high vacuum for 3 h to give the title compound as a white solid (1.33 g, 5.83 mmol, 78%), mp 67-69° C.

$^1$H-NMR (DMSO-d$_6$): 7.30-7.28 (2H, d, 2×C-3H), 7.21-7.19 (2H, d, 2×C-2H), 4.64 (1 H, br, s, OH), 4.41 (2H, s, C-6H$_2$), 3.48-3.45 (2H, t, C-9H$_2$), 3.03-2.99 (2H, m, C-7H$_2$), 2.31 (3H, s, C-1H$_3$), 1.84-1.77 (2H, m, C-8H$_2$).

$^{13}$C-NMR (DMSO-d$_6$): 137.64 (C-2), 130.78 (C-3), 129.01 (C-4), 125.75 (C-5), 58.90 (C-9), 57.64 (C-6), 48.08 (C-7), 24.48 (C-8), 20.70 (C-1).

IR (KBr): 3490, 2969, 2941, 2879, 1510, 1440, 1395, 1376, 1297, 1281, 1253, 1216, 1132, 1060, 1034, 886, 819, 766, 721 cm$^{-1}$

HR-MS: For C$_{11}$H$_{16}$O$_3$S requires 228.0820. found 228.0822.

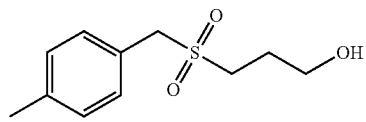

3-(4-Methyl benzylsulfonyl)propyl methanesulfonate

Methanesulfonyl chloride (0.540 mL, 6.95 mmol) was added at 0° C. under nitrogen to a solution of 3-(4-methylbenzylsulfonyl)propan-1-ol (1.329 g, 5.82 mmol) and NEt$_3$ (1 ml, 3.98 mmol) in DCM (40 ml, anhydrous). The solution was stirred at 0° C. for 1 h, and then warmed to room temperature. Stirring was continued for a further 72 h. After this time the solution was extracted with NaHCO$_3$ (2×100 ml) and brine (50 ml), the organic layers were combined, dried (MgSO$_4$) and concentrated under reduced pressure to give the title compound as a pale orange liquid which crystallised upon standing and drying under vacuum. The required product was obtained as an orange solid (1.158 g, 3.78 mmol, 65%), mp 72-74° C.

$^1$H-NMR (DMSO-d$_6$): 7.31-7.29 (2H, d, 2×C-3H), 7.22-7.20 (2H, d, 2×C-4H), 4.47 (2H, s, C-6H$_2$), 4.30-4.27 (2H, t, C-9H$_2$), 3.17 (3H, s, C-10H$_3$), 3.14-3.10 (2H, m, C-7H$_2$), 2.31 (3H, s, C-1H$_3$), 2.12-2.05 (2H, m, C-8H$_2$).

$^{13}$C-NMR (DMSO-d$_6$): 137.76 (C-2), 130.82 (C-4), 129.06 (C-3), 125.41 (C-5), 68.31 (C-9), 57.60 (C-6), 47.17 (C-7), 36.60 (C-10), 21.49 (C-1), 20.71 (C-8).

IR (KBr): 3025, 3986, 2977, 2927, 1786, 1724, 1614, 1515, 1444, 1412, 1354, 1340, 1313, 1280, 1237, 1175, 1134, 1121, 980, 928, 853, 815, 766, 732, 713 cm$^{-1}$

HR-MS: For C$_{12}$H$_{18}$O$_6$S$_2$ requires 306.0596. found 306.0599.

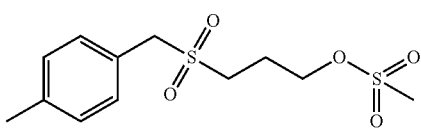

2-[(3-Fluorobenzyl)sulfanyl]ethanol 1-(Bromomethyl)-3-fluorobenzene (1.00 g, 5.29 mmol) was dissolved in acetone (10 mL) to which 2-sulfanylethanol (0.413 g, 5.29 mmol) was added followed by K$_2$CO$_3$ (1.097 g, 7.94 mmol, 1.5 molar equivalent). The reaction mixture was stirred at room temperature for 48 h. The solvent was removed under reduced pressure and the crude material was extracted with DCM and water. The organic layer was collected, dried (MgSO$_4$), filtered and the solvent removed under reduced pressure to give the required product as a pale yellow oil (0.945 g, 96%).

IR (NaCl): 3395, 1616, 1589, 1485, 1446, 1267, 1138, 1061, 1013, 942, 884, 787 cm$^{-1}$ $^1$H NMR (DMSO-d$_6$): 7.16-7.13 (1H, m), 7.08-7.03 (3H, m), 4.77 (1H, t, J=5.5 Hz), 3.75 (2H, s), 3.51-3.46 (2H, m), 2.48 (2H, t, J=6.9 Hz).

HRESIMS: Found: 187.05874 calculted for C$_6$H$_{12}$OF$^{32}$S 187.05874.

Reference 1: Czobor, Francisc; Cristescu, Carol. as-Triazine derivatives with potential therapeutic action. Part XXIX. Synthesis of 5-[2-(halogenobenzylthio)-ethyl]thio-6-azauracil derivatives as potential antiviral agents. Revue Roumaine de Chimie (2002), Volume Date 2001, 46(9), 1007-1011.

Reference 2: Kuliev, A. M.; Sultanov, Yu. M.; Aliev, I. A.; Mekhraliev, N. A. Synthesis of different derivatives of m-fluorobenzyl mercaptan. Katalit. Prevrashcheniya Organ. Soedin., Baku (1981), 51-55.

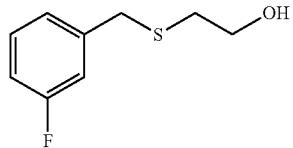 [SMILES: OCCSCc1cccc(F)c1]

2-[(3-Fluorobenzyl)sulfonyl]ethanol

[A]: 2-[(3-Fluorobenzyl)sulfanyl]ethanol (0.945 g, 5.07 mmol) was dissolved in DCM (25 mL, dry) to which m-CPBA (1.921 g, 11.13 mmol, 2.2 molar equivalent) was added at room temperature with stirring. The reaction was slightly exothermic. The reaction mixture was left stirring at room temperature overnight. 15 minutes after the addition of m-CPBA white solid material precipitated. The solid material was filtered off and the filtrate extracted with NaHCO$_3$ (saturated). The organic layer was collected, dried (MgSO$_4$), filtered, and the solvent removed under reduced pressure. The crude product was purified by column chromatography using only ethyl acetate as eluant (R$_F$=0.1). The product was obtained as white crystals (0.725 g, 66%), mp 92-94° C.

IR (NaCl): 3484, 1592, 1487, 1449, 1309, 1266, 1147, 1114, 1072, 842, 793, 748 cm$^{-1}$ $^1$H NMR (DMSO-d$_6$): 7.43-7.41 (1H, m), 7.26-7.21 (3H, m), 5.24 (1H, t, J=5.1 Hz), 4.52 (2H, s), 3.83 (2H, q, J=5.8 Hz), 3.18 (2H, t, J=5.8 Hz).

HRESIMS: Found: 219.04871 calculted for C$_9$H$_{12}$O$_3$F$^{32}$S 219.04857.

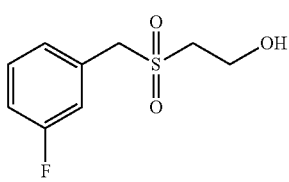 [SMILES: O=S(=O)(CCO)Cc1cccc(F)c1]

2-[(3-Fluorobenzyl)sulfonyl]ethyl methanesulfonate and 1-fluoro-3-[(vinylsulfonyl)methyl]benzene 2-[(3-Fluorobenzyl)sulfonyl]ethanol (0.725 g, 3.18 mmol) was dissolved in DCM (25 mL, dry) to which methane sulfonyl chloride (mesyl chloride) (0.364 g, 3.18 mmol) and TEA (0.482 g, 4.77 mmol, 1.5 molar equivalent) were added at room temperature with stirring. The stirring was continued for 48 h at room temperature. The reaction mixture was extracted with sodium hydrogen carbonate (saturated), dried (MgSO$_4$), filtered and the solvent removed. The clear solution solidified at room temperature to give cream-coloured semi-solid material (900 mg), which was a mixture of two compounds as shown by $^1$H-NMR and TLC. No yield could be calculated for this mixture and no melting point could be measured.

HRESIMS: Found: 201.03806 calculated for C$_9$H$_{10}$O$_2$F$^{32}$S 201.03801.

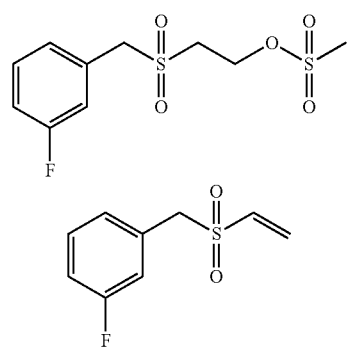

2-[(4-Fluorobenzyl)sulfonyl]ethanol 1-(Bromomethyl)-4-fluorobenzene (1.00 g, 5.29 mmol) was dissolved in DCM (10 mL, dry) to which 2-sulfanyle-thanol (0.413 g, 5.29 mmol) was added followed by K$_2$CO$_3$ (1.097 g, 7.94 mmol, 1.5 molar equivalent). The reaction mixture was stirred at room temperature for 72 h. The reaction mixture was diluted with DCM and water. After extraction the organic layer was collected, dried (MgSO$_4$), filtered and the solvent removed under reduced pressure to give the crude material which was purified by column chromatography using ethyl acetate/n-hexane (1/2) as eluant, R$_F$=0.3. The required product was obtained as pale yellow oil (0.900 g, 91%).

IR (NaCl): 3390, 1601, 1508, 1223, 1157, 1047, 1016, 837, 757, 732 cm$^{-1}$ $^1$H-NMR (DMSO-d$_6$): 7.31-7.28 (2H, m), 7.03-6.70 (2H, m), 3.72 (2H, s), 3.71 (2H, t, J=6.0 Hz), 2.66 (2H, t, J=5.8 Hz).

HRESIMS: Found: 203.05370 calculated for C$_3$H$_{12}$O$_2$F$_1^{32}$S, 203.05366.

Czobor, Francisc; Cristescu, Carol. as-Triazine derivatives with potential therapeutic action. Part XXIX. Synthesis of 5-[2-(halogenobenzylthio)-ethyl]thio-6-azauracil derivatives as potential antiviral agents. Revue Roumaine de Chimie (2002), 46(9), 1007-1011.

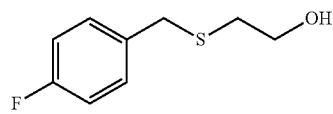 [SMILES: OCCSCc1ccc(F)cc1]

2-[(4-Fluorobenzyl)sulfonyl]ethanol

2-[(4-Fluorobenzyl)sulfanyl]ethanol (1.230 g, 6.60 mmol) was dissolved in DCM (25 mL, dry) to which m-CPBA (2.507 g, 14.53 mmol, 2.2 molar equivalent) was added at room temperature with stirring. The reaction was slightly exothermic. The reaction mixture was left stirring at room temperature overnight. 15 minutes after the addition of m-CPBA a white solid material precipitated. NaHCO$_3$ (saturated) was added and the reaction mixture was extracted. The organic layer was extracted with brine and collected, dried (MgSO$_4$), filtered, and the solvent removed under reduced pressure.

The crude product was purified by column chromatography using only ethyl acetate as eluant (R$_F$=0.1). The product was obtained as white crystals (1.390 g, 97%), mp 93-95° C.

IR (KBr): 1608, 1511, 1286, 1310, 1245, 1139, 1039, 1015, 842, 815, 780, 763, 729 cm$^{-1}$ $^1$H-NMR (CDCl$_3$): 7.46 (2H, dd, J=5.3 Hz & J=8.6 Hz), 7.13 (2H, t, J=8.6 Hz), 4.34 (2H, s), 4.14 (2H, t, J=5.3 Hz), 3.11 (2H, t, J=5.3 Hz).

HRESIMS: Found: 219.04861 calculated for C$_9$H$_{12}$O$_3$F$_1^{32}$S, 219.04857.

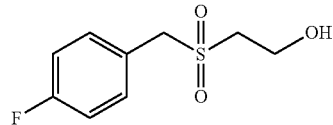 [SMILES: O=S(=O)(CCO)Cc1ccc(F)cc1]

1-Fluoro-4-[(vinylsulfonyl)methyl]benzene

2-[(4-Fluorobenzyl)sulfonyl]ethanol (1.060 g, 4.90 mmol) was dissolved in DCM (25 mL, dry) to which N-methylmorpholine (0.743 g, 7.35 mmol, 1.5 molar equivalent, anhydrous) was added followed by methylsulphonyl chloride (0.842 g, 7.35 mmol, 1.5 molar equivalent) at room temperature with stirring. The stirring was continued at room temperature overnight. The reaction mixture was basified with sodium hydrogen carbonate (saturated). The organic layer was collected after the extraction, dried over (MgSO$_4$), filtered and the solvent removed under reduced pressure. The crude product was applied to a column chromatography using ethyl acetate/n-hexane (1/1, R$_F$=0.5). The product was obtained as white solid (0.650 g, 66%), mp 92-95° C.

IR (KBr): 1604, 1512, 1309, 1262, 1162, 1122, 983, 890, 847, 776, 711 cm$^{-1}$ $^1$H-NMR (CDCl$_3$): 7.37 (2H, dd, J=5.2 Hz & J=3.5 Hz), 6.55 (1H, dd, J=10.0 Hz, J=16.6 Hz), 6.34 (1H, d, J=16.6 Hz), 6.14 (1H, d, J=10.0 Hz), 4.22 (2H, s).

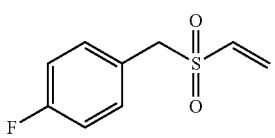

Tested Compounds

N,N,N-trimethyl-2-1(4-bromobenzyl)sulfonyl{ethanaminium methane sulfonate [S1]

2-[(4-Bromobenzy)lsulfonyl]ethyl methanesulfonate (0.06 g, 0.17 mmol) was suspended in trimethylamine (5 ml in toluene) and the mixture was stirred at room temperature, under nitrogen for a period of 5 d, then heated to 60° C. for 20 h. The solvent was concentrated under reduced pressure to give an off-white solid (0.045 g, 0.14 mmol, 83%), m.p. 187-188° C.

$^1$H NMR (DMSO-$d_6$): 7.66-7.64 (2H, d, 2×C(3)H), 7.40-7.38 (2H, d, 2×C(2)H), 4.64 (2H, s, C(5)H$_2$), 3.85-3.80 (2H, m, C(6)H$_2$), 3.78-3.74 (2H, m, C(7)H$_2$), 3.12 (9H, s, C(8)H$_3$, C(9)H$_3$, C(10)H$_3$).

$^{13}$C NMR (DMSO-$d_6$): 133.1 (C-3), 131.6 (C-2), 126.3 (C-1), 121.9 (C-4), 57.6 (C-7), 57.4 (C-5), 52.5 (C-8, C-9, C-10), 44.2 (C-6).

IR (KBr): 3421, 3029, 3002, 2941, 1591, 1489, 1424, 1413, 1360, 1318, 1277, 1193, 1140, 1068, 1040, 1011, 790, 770, 637, 565, 550 cm$^{-1}$

HR-MS: For $C_{12}H_{19}BrNO_2S$ requires 320.0320/322.0300. found 320.0321/322.0297.

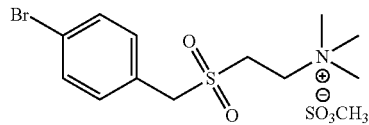

N-{2-[(4-Bromobenzyl)sulfonyl]ethyl}-N,N-dimethylamine [S3]

1-Bromo-4-[(vinylsulfonyl)methyl]benzene (1.600 g, 6.12 mmol) was dissolved in DCM (25 mL, dry) to which dimethylamine (4 mL, 2M in THF) was added at room temperature with stirring. The stirring was continued at room temperature overnight. The reaction mixture was extracted with a saturated solution of sodium carbonate. The organic layer was collected, dried over (MgSO$_4$), filtered and the solvents were removed under reduced pressure after which the crude product was applied to a silica gel column chromatography using ethyl acetate/n-hexane (1/1) in the first instance, followed by ethyl acetate/methanol (9/2, $R_F$=0.5). The product was obtained as a white solid material (1.360 g, 73%) after trituration with n-hexane, mp 58-60° C.

$^1$H-NMR (DMSO-$d_6$): 7.64-7.60 (2H, d, 2×C(4)H), 7.37-7.34 (2H, d, 2×C(3)H), 4.52 (2H, s, C(6)H$_2$), 3.22-3.19 (2H, t, C(7)H$_2$), 2.67-2.63 (2H, t, C(8)H$_2$), 2.17 (6H, s, 2×C(9)H$_3$).

$^{13}$C-NMR (DMSO-$d_6$): 133.1 (C-4), 131.4 (C-3), 127.9 (C-2), 121.9 (C-5), 57.9 (C-6), 51.6 (C-8), 49.4 (C-7), 44.7 (C-9).

IR (KBr): 3424, 2979, 2942, 2822, 2772, 1591, 1488, 1408, 1295, 1275, 1118, 1051, 1013, 843, 816, 640, 513 cm$^{-1}$

HR-MS: Found 305.0081/307.0066 for $C_{11}H_{16}BrNO_2S$ requires 305.0085/307.0065.

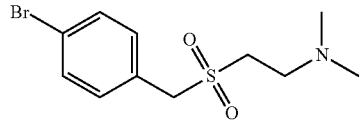 [SMILES: CN(C)CCS(=O)(=O)Cc1ccc(Br)cc1]

N,N-Dimethyl-2-[(4-methylbenzyl)sulfonyl]ethanamine [S4]

2-[(4-Methylbenzyl)sulfonyl]ethyl methanesulfonate and 1-methyl-4-[(vinylsulfonyl)methyl]benzene (4.880 g) were dissolved in DCM (50 mL, dry) to which dimethylamine (4 mL, 2M in THF) was added at room temperature with stirring. The stirring was continued at room temperature overnight after which the reaction mixture was extracted with a saturated solution of sodium carbonate. The organic layer was collected, dried over (MgSO$_4$), filtered and the solvents were removed under reduced pressure and the crude product was applied to a silica gel column chromatography using ethyl acetate/n-hexane (1/1, $R_F$=0.1) in the first instance, followed by ethyl acetate/methanol (9/1). The product was obtained as white solid material (2.200 g, 63% based on 2-[(4-Methylbenzyl)sulfonyl]ethanol) after trituration with n-hexane, mp 68-70° C.

$^1$H-NMR (DMSO-$d_6$): 7.28-7.26 (2H, d, 2×C(2)H, J=8.0 Hz), 7.21-7.19 (2H, d, 2×C(3)H, J=8.0 Hz), 4.44 (2H, s, C(6)H$_2$), 3.17-3.14 (2H, t, C(7)H$_2$, J=14.3 Hz), 2.65-2.61 (2H, t, C(8)H$_2$, J=14.3 Hz), 2.31 (3H, s, C(1)H$_3$), 2.16 (6H, s, 1×C(9)H$_3$, 1×C(10)H$_3$).

$^{13}$C-NMR (DMSO-$d_6$): 137.7 (C-2), 130.8 (C-4), 129.0 (C-2), 125.4 (C-5), 58.4 (C-6), 51.6 (C-7), 49.0 (8), 44.9 (C-9, C-10), 20.7 (C-1).

IR (KBr): 2978, 2813, 2764, 1920, 1511, 1463, 1399, 1380, 1314 (s), 1258, 1156, 1119 (s), 1050, 892, 853, 822, 749, 688, 564, 518, 471 cm$^{-1}$

HR-MS: Found 241.1139 for $C_{12}H_{19}NO_2S$ requires 241.1136.

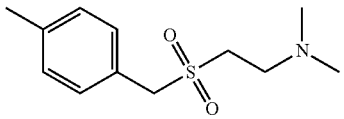

N,N,N-trimethyl-2-[(4-methylbenzyl)sulfonyl]ethanaminium iodide [S5]

N,N-Dimethyl-2-[(4-methylbenzyl)sulfonyl]ethanamine (0.950 g, 3.94 mmol) was dissolved in DCM (25 mL, dry) to which iodomethane (4 mL) was added with stirring at room temperature. The stirring was continued overnight and then the white solid material was filtered of and dried under reduced pressure (1.490 g, 99%), mp 212-214° C.

$^1$H-NMR (DMSO-$d_6$): 7.33-7.31 (2H, d, 2×C(4)H), 7.25-7.23 (2H, d, 2×C(3)H), 4.58 (2H, s, C(6)H$_2$), 3.83-3.79 (2H, m, C(7)H$_2$), 3.74-3.71 (2H, m, C(8)H$_2$), 3.12 (9H, s, 3×C(9)H$_3$), 2.33 (3H, s, C(1)H$_3$).

$^{13}$C NMR (DMSO-$d_6$): 138.17 (C-2), 131.00 (C-4), 129.24 (C-3), 124.38 (C-5), 57.98 (C-8), 57.36 (C-9), 52.50 (C-6), 45.03 (C-7), 18.66 (C-1).

IR (KBr): 3436, 3010, 2937, 3899, 1514, 1486, 1326 (s), 1257, 1153, 1123, 1015, 882, 550, 523, 495 cm$^{-1}$

HR-MS: Found 256.1375 for $C_{13}H_{22}NO_2S$ requires 256.1371.

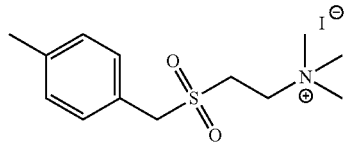

1-(2-[(4-Methylbenzyl)sulfonyl]ethyl)pyrrolidine S7

The mixture of 2-[(4-Methylbenzyl)sulfonyl]ethyl methanesulfonate and 1-methyl-4-[(vinylsulfonyl)methyl]benzene (0.13 g, 0.45 mmol) was dissolved in DCM (15 ml). To this mixture was added pyrrolidine (0.750 mL, 9 mmol, 20 eq.) and the mixture was stirred at room temperature, under nitrogen for 72 h. The crude material was then extracted with NaHCO$_3$ (50 ml) and DCM (50 ml). The organic extracts were collected, dried over MgSO$_4$, filtered and concentrated under reduced pressure to give the title compound as a colourless oil, which crystallised upon standing (0.096 g. 0.36 mmol, 81%), mp 84-86° C.

$^1$H-NMR (DMSO-d$_6$): 7.28-7.26 (2H, d, 2×C(4)H), 7.21-7.19 (2H, d, 2×C(3)H), 4.50 (2H, s, C(6)H$_2$), 3.20-3.16 (2H, t, C(7)H$_2$), 2.80-2.77 (2H, t, C(8)H$_2$), 2.48-2.44 (4H, m, 2×C(9)H$_2$), 1.69-1.65 (4H, m, 2×C(10)H$_2$).

$^{13}$C-NMR (DMSO-d$_6$): 137.7 (C-2), 130.9 (C-4), 129.0 (C-3), 125.4 (C-5), 58.3 (C-6), 53.2 (C-9), 50.3 (C-8), 48.0 (C-7), 23.1 (C-1, C-10).

IR (KBr): 3437, 2971, 2781, 1629, 1515, 1404, 1383, 1312, 1257, 1160, 1120, 1025, 891, 823, 558, 497 cm$^{-1}$

HR-MS: Found 267.1290 for $C_{14}H_{21}NO_2S$ requires 267.1293.

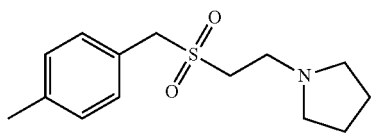 [SMILES: Cc1ccc(CS(=O)(=O)CCN2CCCC2)cc1]

1-Methyl-1-{2-[(4-methylbenzyl)sulfonyl]ethyl}pyrrolidinium iodide [S8]

1-{2-[(4-Methylbenzyl)sulfonyl]ethyl}pyrrolidine (42.4 trig, 0.16 mmol) was dissolved in DCM (3 ml) to which methyl iodide (0.200 mL, 3.2 mmol, 20 eq.) was added. The mixture was stirred at room temperature for a period of 24 h. The yellow precipitate was filtered and dried under reduced pressure (40° C./0.1 mm Hg) for 3 h, to give the title compound as a pale yellow solid (0.033 g, 0.08 mmol, 51%), mp 214-216° C.

$^1$H-NMR (DMSO-d$_6$): 7.33-7.31 (2H, d, 2×C(4)H), 7.25-7.23 (2H, d, 2×C(3)H), 4.58 (2H, s C(6)H$_2$), 3.84-3.80 (21-1, m, C(7)H$_2$), 3.78-3.74 (2H, m, C(8)H$_2$), 3.56-3.48 (4H, 2×C(9)H$_2$), 3.04 (3H, s, C(11)H$_3$), 2.33 (311, s, C(1)H$_3$), 2.17-2.05 (4H, 2×C(10)H$_2$).

$^{13}$C NMR (DMSO-d$_6$): 138.2 (C-2), 131.0 (C-4), 129.2 (C-3), 124.4 (C-5), 63.9 (C-9), 57.9 (C-6), 55.6 (C-8), 47.9 (C-11), 45.8 (C-1), 21.1 (C-10), 18.61 (C-1).

IR (KBr): 3436, 2975, 2909, 1512, 1455, 1313, 1129, 1050, 928, 822, 774, 573, 510 cm$^{-1}$

HR-MS: Found 282.1535 for $C_{15}H_{24}NO_2S$ requires 282.1528.

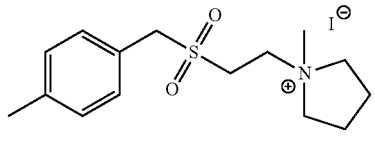 [SMILES: Cc1ccc(CS(=O)(=O)CC[N+]2(C)CCCC2)cc1 ; [I-]]

1-{2-[(4-bromobenzyl}sulfonyl]ethyl}pyrrolidine [S9]

2-[(4-Bromobenzyl)sulfonyl]ethyl methanesulfonate (0.115 g, 0.32 mmol) was placed in a three-necked round bottom flask to which DCM (12 ml) was added. Pyrrolidine (0.590 mL, 7.1 mmol, 22 eq.) was then added and the mixture was stirred at room temperature, under nitrogen for 24 h. The mixture was then extracted with NaHCO$_3$, (100 ml) and DCM (100 ml). The organic layers were collected, dried (MgSO$_4$), filtered and concentrated under reduced pressure to yield the title compound as a pale yellow solid (0.064 g, 0.19 mmol, 60%), mp 90-92° C.

$^1$H-NMR (DMSO-d$_6$): 7.62-7.60 (2H, d, 2×C(4)H), 7.35-7.33 (2H, d, 2×C(3)H), 4.52 (2H, s, C(6)H$_2$), 3.18-3.15 (2H, t, C(7)H$_2$), 2.83-2.79 (2H, t, C(8)H$_2$), 2.50-2.47 (4H, m, 2×C(9)H$_2$), 1.69-1.67 (4H, m, 2×C(10)H$_2$).

$^{13}$C-NMR (DMSO-d$_6$): 133.1 (C-4), 131.4 (C-3), 127.9 (C-2), 121.9 (C-5), 57.8 (C-6), 53.2 (C-9), 50.6 (C-8), 48.0 (C-7), 23.1 (C-10).

IR (KBr): 3421, 2964, 2801, 1590, 1486, 1416, 1294, 1275, 1185, 1145, 1121, 1012, 887, 814, 753 cm$^{-1}$

HR-MS: Found 331.0240/333.0228 for $C_{13}H_{18}BrNO_2S$ requires 331.0242/333.0221.

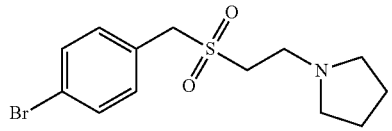 [SMILES: O=S(=O)(CCN1CCCC1)Cc1ccc(Br)cc1]

1-Methyl-1-{2-[(4-bromobenzyl)sulfonyllethyl]}pyrrolidinium iodide [S10]

1-{2-[(4-Bromobenzyl}sulfonyl]ethyl}pyrrolidine JH S9 (20 mg, 0.06 mmol) was 15 dissolved in DCM (4 ml) to which methyl iodide (0.250 mL, 0.57 g, 4.0 mmol) was added. The reaction mixture was stirred at room temperature for 72 h. The resulting precipitate was filtered under reduced pressure to give a pale yellow solid (0.018 g, 0.04 mmol, 62%), mp 196-198° C.

$^1$H-NMR (DMSO-d$_6$): 7.67-7.65 (2H, d, 2×C-2H), 7.39-7.37 (2H, d 2×C-3H), 4.64 (2H, s, C-5H$_2$), 3.85-3.77 (4H, m, C-6H$_2$, C-7H$_2$), 3.56-3.51 (4H, m, 2×C-9H$_2$), 3.04 (3H, s, C-8H$_3$), 2.11-2.06 (4H, m, 2×C-10H$_2$).

IR (KBr): 3436, 2935, 3902, 1712, 1656, 1569, 1487, 1450, 1319, 1256, 1127, 1092, 1014, 809, 743 cm$^{-1}$

HR-MS: For $C_{14}H_2BrNO_2S$ requires 346.0476/348.0456. found 346.0475/348.0457.

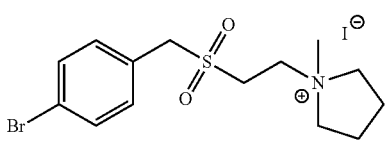 [SMILES: C[N+]1(CCS(=O)(=O)Cc2ccc(Br)cc2)CCCC1 ; [I-]]

4-{3-[(4-methylbenzyl)sulfonyl]propyl}morpholine [S19]

3-[(4-methylbenzyl)sulfonyl]propyl methanesulfonate (0.426 g, 1.39 mmol) was dissolved in DCM (25 mL, dry) to which morpholine (150 mg, 0.150 mL, 1.68 mmol) was added at room temperature with stirring. The reaction mixture was heated under reflux for 48 h. The cold reaction mixture was extracted with a saturated solution of sodium carbonate. The organic layer was collected, dried (MgSO$_4$), filtered and the solvent removed under reduced pressure to give the crude product, which was purified by column chromatography using ethyl acetate ($R_F$=0.2). The required product was obtained as white solid (205 mg, 50%), mp 92-93° C.

$^1$H-NMR (DMSO-d$_6$): 7.30-7.28 (2H, d, 2×C-3H), 7.21-7.19 (21-1, d, 2×C-4H), 4.42 (2H, s, C-6H$_2$), 3.56-3.53 (4H, m, 2×C-11H$_2$), 3.31 (3H, s, C-1H$_3$), 3.03-2.99 (2H, m, C-7H$_2$), 2.35-2.31 (6H, m, 2×C-10H$_2$, 2×C-9H$_2$), 1.85-1.77 (2H, m, C-8H$_2$).

$^{13}$C-NMR (DMSO-d$_6$): 137.66 (C-2), 130.76 (C-4), 129.00 (C-3), 125.74 (C-5), 66.12 (C-11), 57.45 (C-6), 56.03 (C-9), 52.98 (C-10), 48.87 (C-7), 20.70 (C-1), 18.55 (C-8). IR (KBr) 3434, 2952, 2917, 2851, 2824, 1514, 1450, 1355, 1300, 1283, 1149, 1114, 1013, 947, 897, 859, 801, 713, 554, 527, 490 cm$^{-1}$

HR-MS: For C$_{15}$H$_{23}$NO$_3$S requires 297.1399. found 297.1397

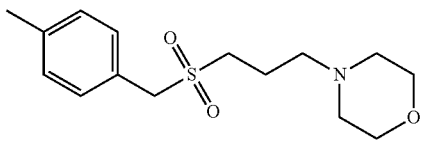 [SMILES: Cc1ccc(CS(=O)(=O)CCCN2CCOCC2)cc1]

4-methyl-4-{3-[(4-methyl benzyl)sulfonyl]propyl}morpholin-4-ium iodide [S22]

4-{3-[(4-Methylbenzyl)sulfonyl]propyl}morpholine (200 mg, 0.673 mmol) was dissolved in DCM (5 mL, dry) to which iodomethane (0.700 mL) was added at room temperature with stirring. The reaction mixture was left standing at room temperature for a week. The white solid material precipitated was filtered and dried in vacuo to give the required material as an off-white solid (215 mg, 73%), mp 181-183° C.

$^1$H-NMR (DMSO-d$_6$): 7.32-7.30 (2H, d, 2×C-3H, 7.23-7.11 (2H, d, 2×C-4H), 4.52 (2H, s, C-6H$_2$), 3.91-3.90 (4H, m, 2×C-12H$_2$), 3.55-3.51 (2H, m, C-7H$_2$), 3.49-3.44 (4H, m, 2×C-11H$_2$), 3.16 (3H, s, C-10H$_3$), 3.11-3.08 (2H, t, C-9H$_2$), 2.32 (3H, s, C-1H$_3$), 2.19-2.08 (2H, m, C-8H$_2$)

$^{13}$C-NMR (DMSO-d$_6$): 142.54 (C-2), 137.85 (C-4), 130.83 (C-3), 125.32 (C-5), 61.36 (C-12), 59.73 (C-11), 59.07 (C-9), 57.66 (C-6), 47.44 (C-10), 46.46 (C-7), 20.70 (C-1), 14.40 (C-8).

IR (KBr): 3446, 2943, 2963, 2897, 1509, 1485, 1472, 1447, 1344, 1328, 1278, 1239, 1137, 1120, 1067, 970, 915, 778, 734, 707, 598, 511 cm$^{-1}$

HR-MS: For C$_{16}$H$_{26}$I NO$_3$S requires 312.1633. found 312.1369

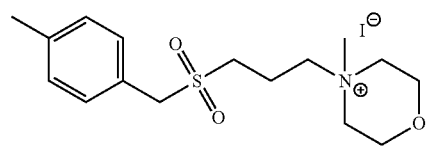 [SMILES: Cc1ccc(CS(=O)(=O)CCC[N+]2(C)CCOCC2)cc1 ; [I-]]

1-{3-[(4-Methylbenzyl)sulfonyl]propyl}-pyrrolidine [S20]

3-(4-Methylbenzylsulfonyl)propyl methanesulfonate (0.22 g, 0.72 mmol) was dissolved in DCM (20 ml, anhydrous) at room temperature to which was added pyrrolidine (1.2 ml, 14.36 mmol, 20 eq.) and the mixture was stirred at room temperature, under nitrogen for 20 h. The solution was then extracted with NaHCO$_3$ (150 ml) and DCM (150 ml), the organic layers were combined, dried (MgSO$_4$) and concentrated under reduced pressure to give the title compound as an orange solid (0.172 g, 0.61 mmol, 85%), mp 84-86° C.

$^1$H-NMR (DMSO-d$_6$): 7.30-7.28 (2H, d, 2×C-3H), 7.21-7.19 (211, d, 2×C-4H), 4.42 (2H, s, C-6H$_2$), 3.04-3.00 (2H, m, C-7H$_2$), 2.46-2.42 (2H, t, C-8H$_2$), 2.40-2.38 (4H, m, 2×C-10H$_2$), 2.31 (3H, s, C-1H$_3$), 1.85-1.78 (2H, m, C-9H$_2$), 1.67-1.65 (4H, m, 2×C-11H$_2$).

$^{13}$C-NMR (DMSO-d$_6$): 137.64 (C-2), 130.77 (C-4), 129.01 (C-3), 125.73 (C-5), 57.56 (C-6), 53.61 (C-9), 53.25 (C-10), 49.06 (C-7), 23.06 (C-11), 20.70 (C-1, C-8).

IR (KBr): 3446, 2972, 2957, 2927, 2792, 2777, 2744, 1625, 1512, 1456, 1311, 1258, 1159, 1118, 1023, 887, 822, 700 cm$^{-1}$

HR-MS: For C$_{15}$H$_{23}$NO$_2$S requires 281.1450. found 281.1448.

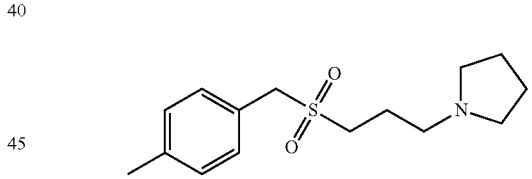

1-Methyl-1-{3-[(4-methylbenzyl)sulfonyl]propyl}pyrrolidinium iodide [S21]

1-{3-[(4-Methylbenzyl)sulfonyl]propyl}-pyrrolidine (0.139 g, 0.49 mmol) was dissolved in DCM (20 ml) at room temperature to which methyl iodide (0.620 mL, 9.96 mmol, 20.3 eq.) was added. The mixture was stirred at room temperature for 20 h prior to being evaporated under reduced pressure. Title compound was obtained as a pale orange amorphous solid (0.108 g, 0.26 mmol, 52%).

$^1$H-NMR (DMSO-d$_6$): 7.32-7.30 (2H, d, 2×C-3H), 7.23-7.21 (2H, d, 2×C-4H), 4.51 (2H, s, C-6H$_2$), 3.53-3.49 (2H, m, C-7H$_2$), 3.45-3.37 (4H, m, 2×C-11H$_2$), 3.12-3.08 (2H, m, C-9H$_2$), 3.01 (3H, s, C-1H$_3$), 2.31 (3H, s, C-1H$_3$), 2.18-2.14 (2H, m, C-8H$_2$), 2.14-2.08 (4H, m, 2×C-12H$_2$).

$^{13}$C-NMR (DMSO-d$_6$): 137.84 (C-2), 130.83 (C-4), 129.12 (C-3), 125.34 (C-5), 63.60 (C-9, C-11), 61.01 (C-6), 57.68 (C-7), 47.59 (C-10), 21.04 (C-1), 20.70 (C-12), 16.37 (C-8).

IR (KBr): 3429, 2932, 1613, 1514, 1455, 1300, 1286, 1209, 1121, 1056, 1004, 934, 823, 765, 702 cm$^{-1}$

HR-MS: For $C_{16}H_{26}I\ NO_2$ requires 296.1684. found 296.1689.

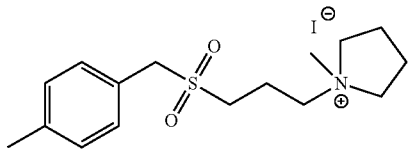 [SMILES: [I-] ; Cc1ccc(CS(=O)(=O)CCC[N+]2(C)CCCC2)cc1]

N-{2-[(3-Fluorobenzyl)sulfonyl]ethyl}-N,N-dimethylamine [S23]

2-[(3-Fluorobenzyl)sulfonyl]ethyl methanesulfonate and 1-fluoro-3-[(vinylsulfonyl)methyl]benzene (900 mg) was dissolved in DCM (8 mL, dry). This solution was divided into four portions, each containing two milliliters.

To the first vial dimethylamine solution (1 mL) (2M in THF) was added at room temperature with stirring. The stirring was continued overnight. The reaction mixture was extracted with sodium hydrogen carbonate (saturated) and DCM. The organic layer was collected, dried (MgSO$_4$), filtered and the solvent removed under reduced pressure. The crude product was purified by column chromatography using ethyl acetate/methanol (100/5) as eluant. The product was obtained as clear oil, which crystallized when left standing at room temperature for a few hours to give the desired product as cream coloured solid (90 mg, 44%), mp 45-47° C. R$_F$=0.2 (ethyl acetate).

IR (KBr): 1592, 1489, 1456, 1287, 1265, 1121, 1062, 1108, 949, 906, 791, 763, 713 cm$^{-1}$ $^1$H-NMR (DMSO-d$_6$): 7.44-7.42 (1H, m), 7.25-7.21 (3H, m), 4.55 (2H, s), 3.22 (2H, t, J=7.3 Hz), 2.65 (2H, t, J=7.3 Hz), 2.16 (6H, s).

HRESIMS: Found: 246.09569 calculted for $C_{11}H_{17}O_2F^{32}S$ 246.09586.

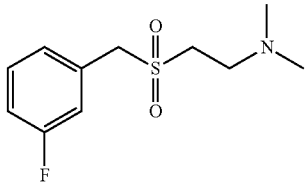 [SMILES: CN(C)CCS(=O)(=O)Cc1cccc(F)c1]

N$^1$-{2-[(3-Fluorobenzyl)sulfonyl]ethyl}-N$^1$,N$^2$,N$^2$-trimethyl-1,2-ethanediamine [S24]

To (2 mL) solution of {2-[(3-fluorobenzyl)sulfonyl]ethyl methanesulfonate and 1-fluoro-3-[(vinylsulfonyl)methyl]benzene} was added N$^1$,N$^1$,N$^2$-trimethyl-1,2-ethanediamine (112 g, 0.371 mmol) at room temperature with stirring. The stirring was continued overnight. The reaction mixture was extracted with sodium hydrogen carbonate (saturated) and DCM. The organic layer was collected, dried (MgSO$_4$), filtered and the solvent removed under reduced pressure. The crude product was purified by column chromatography using ethyl acetate/methanol (100/5) as eluant. The product obtained was purified further by HPLC to give colourless oil (160 mg, 66% based on the alcohol: AIK-23/20) after freeze-drying.

IR (NaCl): 1682, 1594, 1489, 1420, 1319, 1201, 950, 835, 799, 722, 707 cm$^{-1}$.

$^1$H-NMR (DMSO-d$_6$): 7.48-7.44 (1H, m), 7.27-7.23 (3H, m), 4.59 (2H, s), 3.40 (2H, t, J=6.9 Hz), 3.24 (2H, t, J=6.2 Hz), 3.02 (2H, s, br), 2.85 (2H, s, br), 2.78 (6H, s), 2.37 (3H, s).

HRESIMS: Found: 303.15372 calculted for $C_{14}H_{24}O_2N_2F^{32}S$ 303.15370

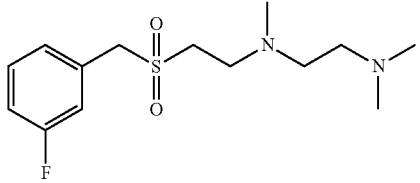 [SMILES: CN(C)CCN(C)CCS(=O)(=O)Cc1cccc(F)c1]

4-{2-[(3-Fluorobenzyl)sulfonyl]ethyl}morpholine [S25]

2-[(3-Fluorobenzyl)sulfonyl]ethyl methanesulfonate and 1-fluoro-3-[(vinylsulfonyl)methyl]benzene (100 mg) was dissolved in DCM (2 mL, dry) to which morpholine (100 μL) was added at room temperature with stirring. The stirring was continued overnight at room temperature. The solvent was removed and the crude material obtained was applied to a silica gel column chromatography. Elution with ethyl acetate, R$_F$=0.2 gave the required product as a white crystalline solid (110 mg, 77%), mp 74-76° C.

IR (KBr): 1613, 1589, 1447, 1300, 1279, 1149, 1112, 1009, 887, 795, 760, 717 cm$^{-1}$ $^1$H-NMR (DMSO-d$_6$): 7.48-7.43 (1H, m), 7.26-7.21 (3H, m), 4.58 (2H, s), 3.58 (4H, t, J=4.6 Hz), 3.29 (2H, t, J=7.0 Hz), 2.71 (2H, t, J=7.1 Hz), 2.41 (4H, t, J=4.4 Hz).

HRESIMS: Found: 288.10645 calculted for $C_{13}H_{19}O_3NF^{32}S$ 288.10642

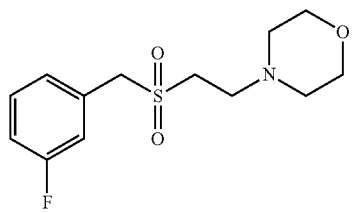 [SMILES: O=S(=O)(CCN1CCOCC1)Cc1cccc(F)c1]

1-{2-[(3-Fluorobenzyl)sulfonyl]ethyl}pyrrolidine [S26]

2-[(3-Fluorobenzyl)sulfonyl]ethyl methanesulfonate and 1-fluoro-3-[(vinylsulfonyl)methyl]benzene (100 mg) was dissolved in DCM (2 mL, dry) to which morpholine (100 μL) was added at room temperature with stirring. The stirring was continued overnight at room temperature. The solvent was removed and the crude material obtained was applied to a silica gel column chromatography. Elution with ethyl acetate, R$_F$=0.1 gave the required product as a white crystalline solid (70 mg, 52%), mp 66-68° C.

IR (KBr): 1593, 1499, 1448, 1316, 1263, 1239, 1119, 947, 889, 803, 753, 689 cm$^{-1}$ $^1$H-NMR (DMSO-d$_6$): 7.48-7.42 (1H, m), 7.25-7.21 (3H, m), 4.56 (2H, s), 3.25 (2H, t, J=7.0 Hz), 2.81 (2H, t, J=7.3 Hz), 2.47 (4H, m), 1.69 (4H, t, J=3.1 Hz).

HRESIMS: Found: 272.11154 calculted for $C_{13}H_{19}O_2NF^{32}S$ 272.11151

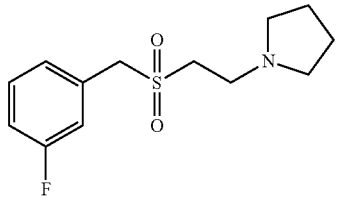 [SMILES: O=S(=O)(CCN1CCCC1)Cc1cccc(F)c1]

N-{2-[(4-Fluorobenzyl)sulfonyl]ethyl}-N,N-dimethylamine [S27]

1-Fluoro-4-[(vinylsulfonyl)methyl]benzene (100 mg, 0.50 mmol) was dissolved in DCM (2 mL, dry) to which dimethylamine (2 mL, 2M in THF) was added at room temperature with stirring. The stirring was continued at room temperature overnight. Solvents were removed under reduced pressure and the crude product was applied to a silica gel column chromatography using ethyl acetate/n-hexane (1/1, $R_F$=0.1) in the first instance, followed by ethyl acetate/methanol (9/1). The product was obtained as white solid material (120 mg, 98%), mp 50-52° C.

IR (KBr): 1606, 1510, 1465, 1415, 1379, 1317, 1221, 1116, 835, 777, 703 $cm^{-1}$ $^1$H-NMR (CDCl$_3$): 7.44 (2H, dd, J=5.2 Hz, & J=8.7 Hz), 7.13 (2H, t, J=8.7 Hz), 4.33 (2H, s), 3.04 (2H, t, J=6.6 Hz), 2.85 (2H, t, J=6.6 Hz), 2.31 (6H, s).

HRESIMS: Found: 246.09569 calculated for $C_{11}H_{17}O_2N_1F_1{}^{32}S_1$ 246.09586.

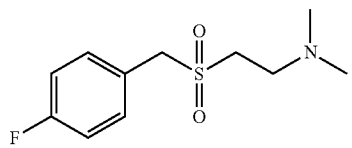 [SMILES: CN(C)CCS(=O)(=O)Cc1ccc(F)cc1]

4-{2-[(4-Fluorobenzyl)sulfonyl]ethyl}morpholine [S28]

1-Fluoro-4-[(vinylsulfonyl)methyl]benzene (100 mg, 0.50 mmol) was dissolved in DCM (2 mL, dry) to which morpholine (66 mg, 0.066 mL, 0.74 mmol) was added at room temperature with stirring. The stirring was continued at room temperature overnight. Solvents were removed under reduced pressure and the crude product was applied to a silica gel column chromatography using ethyl acetate/n-hexane (1/1, $R_F$=0.1) in the first instance, followed by ethyl acetate/methanol (9/1, $R_F$=0.7). The product was obtained as white solid material (130 mg, 91%), mp 72-74° C.

IR (KBr): 1604, 1511, 1464, 1364, 1321, 1278, 1231, 1147, 1116, 890, 849, 777 $cm^{-1}$ $^1$H-NMR (CDCl$_3$): 7.44 (1H, d, J=5.2 Hz), 7.42 (1H, d, J=5.2 Hz), 7.14 (2H, t, J=8.6 Hz), 4.34 (2H, s), 3.76 (4H, br), 3.09 (2H, br), 2.91 (2H, br), 2.55 (4H, br).

HRESIMS: Found: 288.10629 calculated for $C_{13}H_{19}O_3N_1F_1{}^{32}S$, 288.10642.

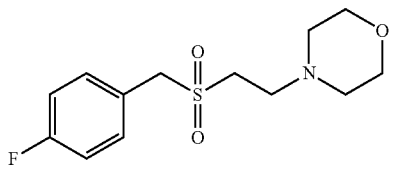 [SMILES: O=S(=O)(CCN1CCOCC1)Cc1ccc(F)cc1]

1-{2-[(4-Fluorobenzyl)sulfonyl]ethyl}pyrrolidine [S29]

1-Fluoro-4-[(vinylsulfonyl)methyl]benzene (100 mg, 0.50 mmol) was dissolved in DCM (2 mL, dry) to which pyrrolidine (44 mg, 0.052 mL, 0.62 mmol) was added at room temperature with stirring. The stirring was continued at room temperature overnight. Solvents were removed under reduced pressure and the crude product was applied to a silica gel column chromatography using ethyl acetate/n-hexane (1/1, $R_F$=0.1) in the first instance, followed by ethyl acetate/methanol (9/1, $R_F$=0.7). The product was obtained as white solid material (125 mg, 92%), mp 76-78° C.

IR (KBr): 1604, 1510, 1460, 1312, 1285, 1230, 1123, 838, 787 $cm^{-1}$ $^1$H-NMR (CDCl$_3$): 7.43 (1H, d, J=5.2 Hz), 7.41 (1H, d, J=5.2 Hz), 7.12 (2H, t, J=8.6 Hz), 4.33 (2H, s), 3.09-2.97 (4H, m), 2.58 (4H, s, br), 1.85 (4H, m).

HRESIMS: Found: 272.11133 calculated for $C_{13}H_{19}O_2N_1F_1{}^{32}S_1$ 272.11151.

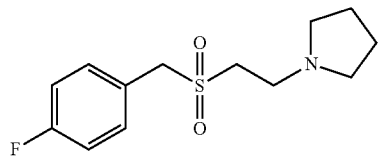 [SMILES: O=S(=O)(CCN1CCCC1)Cc1ccc(F)cc1]

$N^1$-{2-[(4-Fluorobenzyl)sulfonyl]ethyl}-$N^1$,$N^2$,$N^2$-trimethyl-1,2-ethanediamine [S30]

1-Fluoro-4-[(vinylsulfonyl)methyl]benzene (100 mg, 0.50 mmol) was dissolved in DCM (2 mL, dry) to which $N^1$,$N^1$,$N^2$-trimethyl-1,2-ethanediamine (62 mg, 0.062 mL, 0.60 mmol) was added at room temperature with stirring. The stirring was continued at room temperature overnight. Solvents were removed under reduced pressure and the crude product was applied to a silica gel column chromatography using only ethyl acetate in the first instance, followed by ethyl acetate/methanol (1/1, $R_F$=0.1). The product was obtained as pale yellow oil (110 mg, 73%).

IR (KBr): 1682, 1606, 1512, 1422, 1312, 1199, 1125, 837, 798, 722, 707 $cm^{-1}$ $^1$H-NMR (CDCl$_3$): 7.45-7.41 (2H, m), 7.15 (2H, t, J=8.5 Hz), 4.36 (2H, s), 3.41 (2H, br), 3.32 (2H, br), 3.24 (4H, m), 2.93 (6H, s), 2.58 (3H, s).

HRESIMS: Found: 303.15363 calculted for $C_{22}H_{20}F_1$ 303.15436.

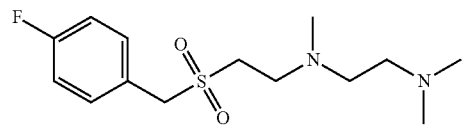 [SMILES: CN(C)CCN(C)CCS(=O)(=O)Cc1ccc(F)cc1]

(S)—N-(2-((3-fluorobenzyl)sulfonyl)ethyl)butan-2-amine [S31]

1-Fluoro-3-[(vinylsulfonyl)methyl]benzene (50 mg) was dissolved in DCM (2 mL, dry) to which (S)-butan-2-amine (0.050 mL) was added at room temperature with stirring. The stirring was continued overnight at room temperature. The solvent and excess amine was removed by rotary evaporation to give the desired product as yellow oil (81 mg, 87%).

IR (KBr): 2965, 2935, 2866, 1619, 1587, 1487, 1451, 1312, 1304, 1286, 1112, 948, 793 cm$^{-1}$ $^1$H-NMR (CDCl$_3$): 7.42-7.35 (1H, m), 7.25-7.17 (2H, m), 7.13-7.08 (1H, m), 4.36 (2H, s), 3.21-3.08 (2H, m), 3.05 (2H, t, J=6.0 Hz), 2.64-2.57 (1H, m), 1.54-1.47 (1H, m), 1.40-1.30 (1H, m), 1.06 (3H, d, J=6.0 Hz), 0.91 (3H, t, J=7.5).

LSESIMS: Found: 274.00 calculted for C$_{13}$H$_{21}$FNO$_2$S$^+$ 274.12

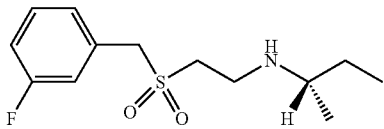 [SMILES: CC[C@H](C)NCCS(=O)(=O)Cc1cccc(F)c1]

(R)—N-(2-((3-Fluorobenzyl)sulfonyl)ethyl)butan-2-amine [S32]

1-Fluoro-3-[(vinylsulfonyl)methyl]benzene (50 mg) was dissolved in DCM (2 mL, dry) to which (R)-butan-2-amine (0.050 mL) was added at room temperature with stirring. The stirring was continued overnight at room temperature. The solvent and excess amine was removed by rotary evaporation, giving the desired product as yellow oil (82 mg, 87%).

IR (KBr): 2962, 2935, 2879, 1591, 1489, 1451, 1315, 1291, 1269, 1239, 1140, 1110, 950, 795 cm$^{-1}$ $^1$H-NMR (CDCl$_3$): 7.42-7.35 (1H, m), 7.25-7.17 (2H, m), 7.13-7.08 (1H, m), 4.36 (2H, s), 3.21-3.08 (2H, m), 3.05 (2H, t, J=6.0 Hz), 2.64-2.57 (1H, m), 1.54-1.47 (1H, m), 1.40-1.30 (1H, m), 1.06 (3H, d, J=6.0 Hz), 0.91 (3H, t, J=7.5).

LSESIMS: Found: 274.07 calculted for C$_{13}$H$_{21}$FNO$_2$S$^+$ 274.12

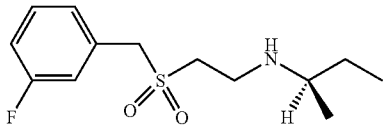 [SMILES: CC[C@@H](C)NCCS(=O)(=O)Cc1cccc(F)c1]

(S)—N-(2-((4-Bromobenzyl)sulfonyl)ethyl)butan-2-amine [S33]

1-Bromo-4-((vinylsulfonyl)methyl)benzene (60 mg) was dissolved in DCM (2 mL, dry) to which (S)-butan-2-amine (0.050 mL) was added at room temperature with stirring. The stirring was continued overnight at room temperature. The solvent and excess amine was removed by rotary evaporation, giving the desired product as yellow oil (78 mg, 81%).

IR (KBr): 2965, 2932, 2876, 1587, 1485, 1403, 1298, 1272, 1121, 1011, 814 cm$^{-1}$ $^1$H NMR (CDCl$_3$): 7.54 (2H, d, J=6.5 Hz), 7.31 (2H, d, J=6.5 Hz), 4.32 (2H, s), 3.20-3.08 (2H, m), 3.02 (2H, t, J=6.0 Hz), 2.62-2.57 (1H, m), 1.54-1.47 (1H, m), 1.40-1.30 (1H, m), 1.05 (3H, d, J=6.0 Hz), 0.91 (3H, t, J=7.5).

LSESIMS: Found: 334.00 calculted for C$_{13}$H$_{21}$BrNO$_2$S$^+$ 334.05

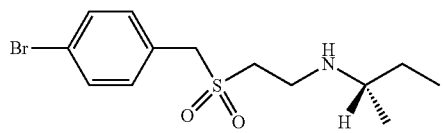 [SMILES: CC[C@H](C)NCCS(=O)(=O)Cc1ccc(Br)cc1]

(R)—N-(2-((4-Bromobenzyl)sulfonyl)ethyl)butan-2-amine [S34]

1-Bromo-4-((vinylsulfonyl)methyl)benzene (60 mg) was dissolved in DCM (2 mL, dry) to which (R)-butan-2-amine (0.050 mL) was added at room temperature with stirring. The stirring was continued overnight at room temperature. The solvent, and excess amine, were removed by rotary evaporation giving the desired product as a yellow oil (80 mg, 82%).

IR (KBr): 2962, 2922, 2872, 1589, 1487, 1300, 1280, 1118, 1071, 1011 cm$^{-1}$ $^1$H NMR (d-CDCl$_3$): 7.54 (2H, d, J=6.5 Hz), 7.31 (2H, d, J=6.5 Hz), 4.32 (2H, s), 3.20-3.08 (2H, m), 3.05 (2H, t, J=6.0 Hz), 2.64-2.56 (1H, m), 1.54-1.47 (1H, m), 1.40-1.30 (1H, m), 1.06 (3H, d, J=6.0 Hz), 0.91 (3H, t, J=7.5).

LSESIMS: Found: 334.00 calculted for C$_{13}$H$_{21}$BrNO$_2$S$^+$ 334.05

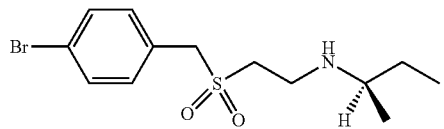 [SMILES: CC[C@@H](C)NCCS(=O)(=O)Cc1ccc(Br)cc1]

Biological Evaluation

The sulfones were first examined for their ability to modulate the cytokine responses of macrophages exposed to pathogen-associated molecular patterns (PAMPs). The PAMPS chosen for the analysis were *Salmonella Minnesota* lipopolysaccharide (LPS), which interacts with the pattern-recognition receptor, Toll-like receptor (TLR) 4 and Pam3CSK4, a synthetic triacylatedlipopeptide (LP) that mimics the acylated amino-terminus of bacterial LPs (BLP) and acts as a TLR1/TLR2 agonist. The cytokines measured were tumour necrosis factor alpha (TNF-α), interleukin 6 (IL-6) and IL-12p40 all of whose secretion can contribute to inflammation.

The effect of different sulfones on the PAMP-induced cytokine responses is shown in Table 1.

TABLE 1

Modulatory effect of the library of sulfones on PAMP-dependent cytokine production in macrophages

| | CYTOKINE | | | | | |
|---|---|---|---|---|---|---|
| | LPS | | | BLP | | |
| SULFONE | IL-12 | TNF-α | IL-6 | IL-12 | TNF-α | IL-6 |
| S1 | | **↓ | | | *↑ | |
| S2 | | **↓ | **↓ | | | |
| S3 | *↓ | | *↓ | | | |
| S4 | **↓ | ***↓ | ***↓ | | | |
| S5 | *↓ | | *↓ | *↓ | | *↓ |
| S7 | **↓ | **↓ | ***↓ | | | |
| S8 | **↓ | ***↓ | | *↓ | | |
| S9 | **↓ | **↓ | | | | |
| S10 | **↓ | | ***↓ | *↓ | *↓ | |
| S12 | | *↓ | | *↑ | | |
| S13 | *↓ | | | *↑ | | **↓ |
| S14 | | | | *↑ | | |
| S15 | **↓ | ***↓ | | | | **↓ |
| S16 | **↓ | | | | | |
| S17 | ***↓ | | | | | |
| S18 | **↓ | | | *↓ | | |
| S19 | | | | | | |
| S20 | | | | | | |
| S21 | | | | | | |
| S22 | | | | | | |
| S23 | *↑ | | | *↑ | | |
| S24 | | | | *↑ | | |
| S25 | | | | *↑ | | |
| S26 | | | *↑ | | | |
| S27 | | | *↓ | | *↓ | |
| S28 | | | *↓ | | **↑ | |

Bone marrow-derived macrophages pre-incubated for 18 h with 1 μg/ml of compounds were stimulated with 100 ng/ml LPS or 10 ng/ml BLP in the continued presence of the compounds. After 24 h, supernatants were collected and measured for their IL-12p40, TNF-α and IL-6 content by ELISA. Student's t-test was used to compare activity of compound (*P<0.05; P<0.01, *P<0.001). Arrows down (↓) indicate significant down-regulation and arrows up (↑) significant up-regulation of the levels of cytokines versus control.

Overall, many of the sulfones showed some evidence of inhibiting pro-inflammatory cytokine production and hence two of them, S3 and S5 were selected for testing for anti-inflammatory activity in a mouse model of rheumatoid arthritis, collagen-induced arthritis (CIA). As can be seen, in FIG. 1 prophylactic treatment with either S3 or S5 significantly suppressed the development of arthritis in these animals.

S3 and S5 were also tested for their effects on another immune system cell type, the mast cell. Similar to macrophages, activation of mast cells for example via the high-affinity receptor for IgE results in degranulation, resulting in release of inflammatory mediators, and secretion of various cytokines. As can be seen in FIG. 2, S3 and S5 are both capable of suppressing degranulation and inhibiting secretion of TNF-α and IL-6.

As a consequence of the mast cell findings S3 and S3 were tested in a mouse model of asthma, ovalbumin-induced airway hypersensitivity (OAH). As can be shown in FIG. 3, both sulfones are able to inhibit infiltration of disease-causing eosinophils into the lungs and also overall lung pathology.

The invention claimed is:

1. A method of modulating an immune response in an individual, the method comprising administering to the individual a compound according to formula (I), or a physiologically acceptable salt, solvate, ester or other physiologically functional derivative thereof:

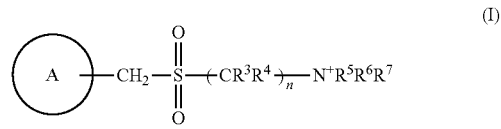

(I)

wherein,

A is an aryl group, optionally substituted by at least one substituent;

where said at least one substituent is independently selected from the group consisting of alkyl, alkenyl, alkynyl, aryl, heteroaryl, carboxy, alkyloxycarbonyl hydroxyl, amino, nitro, alkyloxy, perfluoroalkloxy, —SH, alkylthio, formyl, cyano, carbamoyl, an amide, halo, a ketone, —S(O)NR$^{12}$R$^{13}$ or —S(O)R$^{14}$; wherein R$^{12}$, R$^{13}$ or R$^{14}$ are independently selected from the group consisting of H, alkyl, alkenyl, alkynyl, or substituted or unsubstituted monocyclic or polycyclic aryl or heteroaryl;

wherein when one of R$^5$, R$^6$ and R$^7$ is absent, the nitrogen atom to which they are bonded is not charged or when R$^5$, R$^6$ and R$^7$ are present together the nitrogen atom to which they are bonded is positively charged and there is present a negatively charged counter ion;

R$^3$, R$^4$, R$^5$, R$^6$ and R$^7$ when present are independently, for each occurrence, selected from the group consisting of H, alkyl, alkenyl and alkynyl; and optionally, two or more of R$^5$, R$^6$ and R$^7$ are bonded together to form a monocyclic or bicyclic ring with the nitrogen atom to which they are bonded, wherein when R$^3$, R$^4$, R$^5$, R$^6$ and R$^7$ are independently an alkyl, alkenyl or alkynyl group, and each group is optionally substituted with an amine; and n is an integer having a value of from 1 to 6, in an amount sufficient to modulate the immune response in the individual.

2. A method according to claim 1, wherein
n is 2 or 3
and R$^3$ and R$^4$ are both H.

3. The method according to claim 1 wherein A is substituted with an alkyl, carboxy, alkyloxycarbonyl hydroxyl, amino, nitro, alkyloxy, —SH, alkylthio, formyl, cyano, carbamoyl, or halo.

4. The method according to claim 1, wherein A is a phenyl group.

5. A method of treating an individual in need of therapy, the method comprising administering to the individual a compound of formula (II) or a physiologically acceptable salt, solvate, ester or other physiologically functional derivative

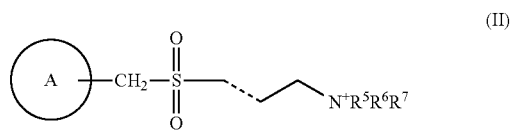

(II)

wherein

A is an phenyl group substituted by at least one substituent;

wherein said at least one optional substituent is independently selected from the group consisting of alkyl, carboxy, alkyloxycarbonyl hydroxyl, amino, nitro, alkyloxy, —SH, alkylthio, formyl, cyano, carbamoyl, halo;

the dashed bond is present or absent;

wherein when one of $R^5$, $R^6$ and $R^7$ is absent, the nitrogen atom to which they are bonded is not charged and both remaining R groups are not H, or when $R^5$, $R^6$ and $R^7$ are present together the nitrogen atom to which they are bonded is positively charged and there is present a negatively charged counter ion;

$R^5$, $R^6$ and $R^7$, when present are independently, for each occurrence, an alkyl, wherein each alkyl group is optionally substituted with an amine; and optionally, two or more of $R^5$, $R^6$ and $R^7$ are bonded together to form a monocyclic ring with the nitrogen atom to which they are bonded, in an amount sufficient to treat the individual.

6. A compound of formula (III) or a physiologically acceptable salt, solvate, ester or other physiologically functional derivative:

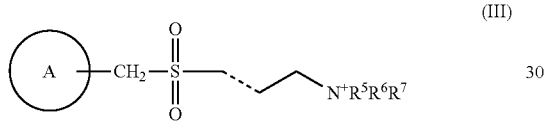

(III)

wherein

A is an phenyl group, substituted by at least one substituent;

wherein said at least one optional substituent is independently selected from the group consisting of alkyl, and halo;

the dashed bond is present or absent;

wherein when one of $R^5$, $R^6$ and $R^7$ is absent, the nitrogen atom to which they are bonded is not charged and both remaining R groups are not H, or when $R^5$, $R^6$ and $R^7$ are present together the nitrogen atom to which they are bonded is positively charged and there is present a negatively charged counter ion; and $R^5$, $R^6$ and $R^7$, when present are independently, for each occurrence, an alkyl, wherein each alkyl group is optionally substituted with an amine; and optionally, two or more of $R^5$, $R^6$ and $R^7$ are bonded together to form a monocyclic ring with the nitrogen atom to which they are bonded.

7. The compound according to claim 6 wherein the substituent on A is methyl, bromine or chlorine.

8. The method according to claim 1, wherein $R^5$, $R^6$ and $R^7$ are present and are each alkyl.

9. The method according to claim 8, wherein $R^5$, $R^6$ and $R^7$ are each methyl.

10. The method according to claim 5, wherein two of $R^5$, $R^6$ and $R^7$ form a pyrrolidine ring or a morpholine ring with the nitrogen atom, and the remainder one of $R^5$, $R^6$ or $R^7$ is a methyl group or is absent.

11. The method according to claim 1, wherein $R^5$, $R^6$ or $R^7$ are present and wherein said negatively charged counter ion is selected from the group consisting of chloride($Cl^-$), bromide($Br^-$), iodide($I^-$) fluoride ($F^-$), and methanesulphonate ($SO_3^-CH_3$).

12. A compound according to claim 6, selected from the group consisting of:

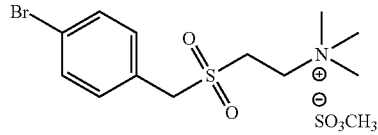

N,N,N-trimethyl-2-1(4-bromobenzyl)sulfonyl {ethanaminium mathane sulfonate

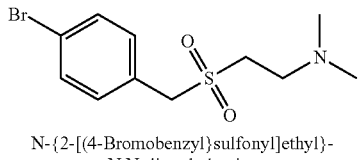

N-{2-[(4-Bromobenzyl)sulfonyl]ethyl}-N,N-dimethylamine

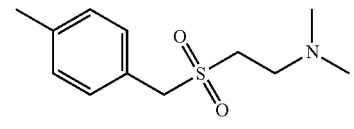

N,N-Dimethyl-2-[(4-methylbenzyl)sulfonyl]ethanamine

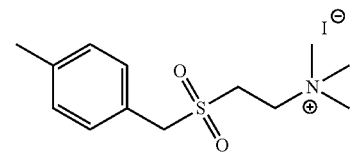

N,N,N-trimethyl-2-[(4-bromobenzyl)sulfonyl]ethanaminium iodide

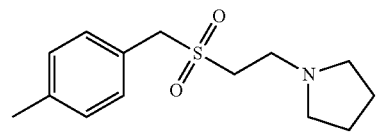

1-(2-[(4-Methylbenzyl)sulfonyl]ethyl)pyrrolidine

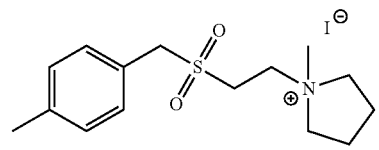

1-Methyl-1-{2-[(4-methylbenzyl)sulfonyl]ethyl}pyrrolidinium iodide

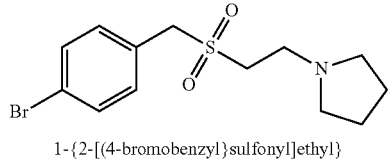

1-{2-[(4-bromobenzyl}sulfonyl]ethyl}pyrrolidinium

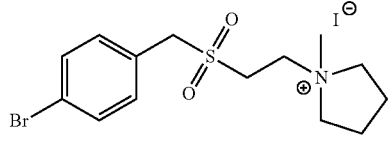

1-Methyl-1-{2-[(4-bromobenzyl}sulfonylethyl]}pyrrolidinium iodide

-continued

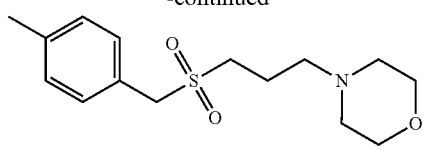
4-{3-[(methylbenzyl)sulfonyl]propyl}morpholine

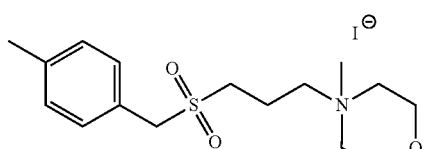
4-methyl-4-{3-[(methylbenzyl)sulfonyl]propyl}morpholine-4-ium iodide

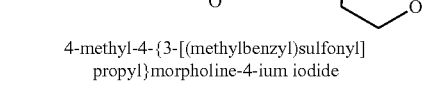
1-{3-[(4-Methylbenzyl)sulfonyl]propyl}-pyrrolidine

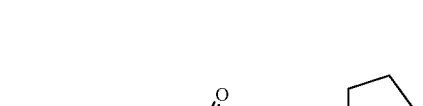
1-Methyl-1-{3-[(4-methylbenzyl)sulfonyl]propyl}pyrrolidinium iodide

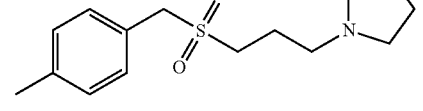
N-{2-[(3-Fluorobenzyl)sulfonyl]ethyl}-N,N-dimethylamine

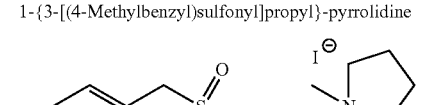
$N^1$-{2-[(3-Fluorobenzyl)sulfonyl]ethyl}-$N^1,N^2,N^2$-trimethyl-1,2-ethanediamine

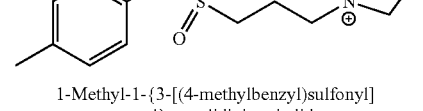
4-{2-[(3-Fluorobenzyl)sulfonyl]ethyl}morpholine

-continued

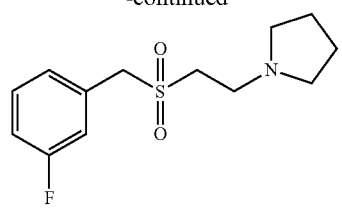
1-{2-[(3-Fluorobenzyl)sulfonyl]ethyl}pyrrolidine

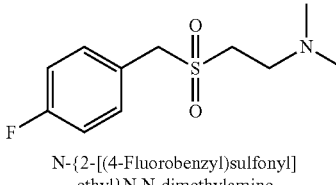
N-{2-[(4-Fluorobenzyl)sulfonyl]ethyl}N,N-dimethylamine

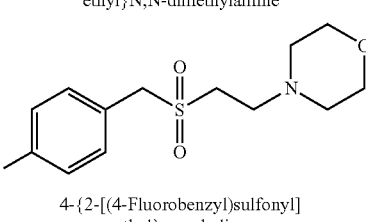
4-{2-[(4-Fluorobenzyl)sulfonyl]ethyl}morpholine

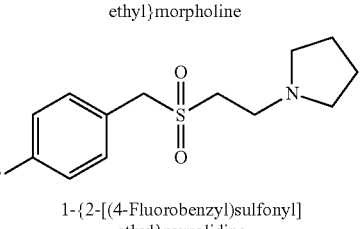
1-{2-[(4-Fluorobenzyl)sulfonyl]ethyl}pyrrolidine

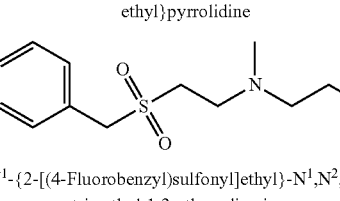
$N^1$-{2-[(4-Fluorobenzyl)sulfonyl]ethyl}-$N^1,N^2,N^2$-trimethyl-1,2-ethanediamine

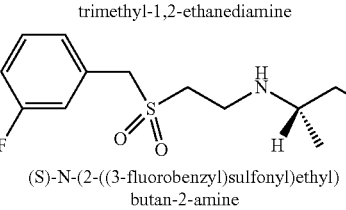
(S)-N-(2-((3-fluorobenzyl)sulfonyl)ethyl)butan-2-amine

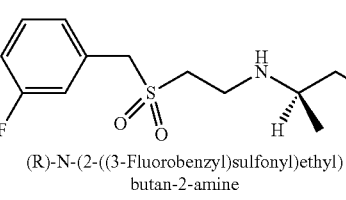
(R)-N-(2-((3-Fluorobenzyl)sulfonyl)ethyl)butan-2-amine

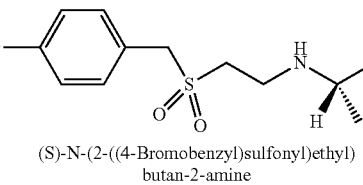
(S)-N-(2-((4-Bromobenzyl)sulfonyl)ethyl)butan-2-amine

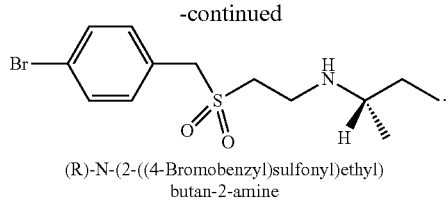

(R)-N-(2-((4-Bromobenzyl)sulfonyl)ethyl)
butan-2-amine

13. The method according to claim 1, wherein said individual is in need of inhibition of the immune response.

14. The method according to claim 11 wherein said individual suffers from an inflammatory disease selected from the group consisting of type 1 diabetes mellitus, rheumatoid arthritis, systemic lupus erythematosus, psoriasis, multiple sclerosis, autoimmune hepatitis, sarcoidosis, inflammatory bowel disease, Crohn's disease, asthma, chronic obstructive pulmonary disease and atherosclerosis.

15. The method according to claim 14, wherein said individual suffers from an inflammatory disease selected from the group consisting of rheumatoid arthritis and asthma.

16. A pharmaceutical composition comprising a compound according to claim 6, together with a pharmaceutically acceptable excipient therefor.

* * * * *